US009161995B2

(12) United States Patent
Guschin et al.

(10) Patent No.: US 9,161,995 B2
(45) Date of Patent: Oct. 20, 2015

(54) METHODS AND COMPOSITIONS FOR ALTERATION OF A CYSTIC FIBROSIS TRANSMEMBRANE CONDUCTANCE REGULATOR (CFTR) GENE

(75) Inventors: Dmitry M. Guschin, Richmond, CA (US); Michael C. Holmes, Richmond, CA (US); David Paschon, Richmond, VA (US); Phillip Tam, Richmond, CA (US)

(73) Assignee: Sangamo BioSciences, Inc., Richmond, CA (US)

( * ) Notice: Subject to any disclaimer, the term of this patent is extended or adjusted under 35 U.S.C. 154(b) by 0 days.

(21) Appl. No.: 13/558,101

(22) Filed: Jul. 25, 2012

(65) Prior Publication Data
US 2013/0145485 A1 Jun. 6, 2013

Related U.S. Application Data

(60) Provisional application No. 61/511,434, filed on Jul. 25, 2011.

(51) Int. Cl.
*C12N 9/00* (2006.01)
*C12N 15/00* (2006.01)
*C12N 15/87* (2006.01)
*C07K 5/00* (2006.01)
*A61K 48/00* (2006.01)
*C12N 15/85* (2006.01)
*C12N 5/0775* (2010.01)
*C12N 9/22* (2006.01)
*C12N 15/90* (2006.01)

(52) U.S. Cl.
CPC .............. *A61K 48/00* (2013.01); *A61K 48/005* (2013.01); *C12N 5/0662* (2013.01); *C12N 9/22* (2013.01); *C12N 15/85* (2013.01); *C12N 15/907* (2013.01); *C07K 2319/81* (2013.01); *C12N 2015/8536* (2013.01); *C12N 2800/30* (2013.01); *C12N 2800/80* (2013.01)

(58) Field of Classification Search
CPC combination set(s) only.
See application file for complete search history.

(56) References Cited

U.S. PATENT DOCUMENTS

| 5,356,802 | A | 10/1994 | Chandrasegaran |
| 5,436,150 | A | 7/1995 | Chandrasegaran |
| 5,487,994 | A | 1/1996 | Chandrasegaran |
| 5,789,538 | A | 8/1998 | Rebar et al. |
| 5,925,523 | A | 7/1999 | Dove et al. |
| 6,007,988 | A | 12/1999 | Choo et al. |
| 6,013,453 | A | 1/2000 | Choo et al. |
| 6,140,081 | A | 10/2000 | Barbas |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,794,136 | B1 | 9/2004 | Eisenberg et al. |
| 6,824,978 | B1 | 11/2004 | Cox, III et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |
| 7,153,949 | B2 | 12/2006 | Kim et al. |
| 7,163,824 | B2 | 1/2007 | Cox, III et al. |
| 7,253,273 | B2 | 8/2007 | Collingwood |
| 7,262,054 | B2 | 8/2007 | Jamieson et al. |
| 7,361,635 | B2 | 4/2008 | Miller et al. |
| 7,888,121 | B2 | 2/2011 | Urnov et al. |
| 2003/0232410 | A1 | 12/2003 | Liljedahl et al. |
| 2005/0026157 | A1 | 2/2005 | Baltimore et al. |
| 2005/0064474 | A1 | 3/2005 | Urnov et al. |
| 2005/0208489 | A1 | 9/2005 | Carroll et al. |
| 2005/0267061 | A1 | 12/2005 | Martin |
| 2006/0063231 | A1 | 3/2006 | Li et al. |
| 2006/0188987 | A1 | 8/2006 | Guschin et al. |
| 2007/0218528 | A1 | 9/2007 | Miller |
| 2008/0131962 | A1 | 6/2008 | Miller |
| 2008/0299580 | A1 | 12/2008 | DeKelver et al. |
| 2009/0054985 | A1 | 2/2009 | Anderson |
| 2009/0068164 | A1 | 3/2009 | Segal et al. |
| 2009/0215878 | A1 | 8/2009 | Tan et al. |

(Continued)

FOREIGN PATENT DOCUMENTS

| GB | 2338237 | 12/1999 |
| WO | WO 95/19431 A1 | 7/1995 |
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |

(Continued)

OTHER PUBLICATIONS

Anson, et al., "Gene Therapy for Cystic Fibrosis Airway Disease—Is Clinical Success Imminent?" *Curr. Gene Ther.*, 6(2):161-179 (2006).

(Continued)

*Primary Examiner* — Maria Leavitt
*Assistant Examiner* — Kimberly A Aron
(74) *Attorney, Agent, or Firm* — Pasternak Patent Law; Susan Abrahamson

(57) ABSTRACT

Nucleases and methods of using these nucleases for alteration of a CFTR gene and generation of cells and animal models.

19 Claims, 8 Drawing Sheets

(56) References Cited

U.S. PATENT DOCUMENTS

| | | | |
|---|---|---|---|
| 2009/0263900 | A1 | 10/2009 | DeKelver et al. |
| 2010/0047805 | A1 | 2/2010 | Wang |
| 2010/0158868 | A1 | 6/2010 | Kan |
| 2011/0023151 | A1* | 1/2011 | Weinstein et al. ............ 800/3 |
| 2011/0086015 | A1 | 4/2011 | McCray et al. |
| 2011/0201055 | A1 | 8/2011 | Doyon et al. |
| 2011/0207221 | A1 | 8/2011 | Cost et al. |
| 2011/0287512 | A1 | 11/2011 | Paschon et al. |
| 2011/0301073 | A1 | 12/2011 | Gregory et al. |
| 2012/0060230 | A1 | 3/2012 | Collingwood et al. |

FOREIGN PATENT DOCUMENTS

| | | | |
|---|---|---|---|
| WO | WO 01/60970 | A2 | 8/2001 |
| WO | WO 01/88197 | A2 | 11/2001 |
| WO | WO 02/16536 | A1 | 2/2002 |
| WO | WO 02/42459 | A2 | 5/2002 |
| WO | WO 02/077227 | A2 | 10/2002 |
| WO | WO 02/099084 | A2 | 12/2002 |
| WO | WO 2005/014791 | A2 | 2/2005 |
| WO | 2007014181 | A2 | 2/2007 |
| WO | WO 2007/014275 | A2 | 2/2007 |
| WO | WO 03/016496 | A2 | 2/2008 |
| WO | WO 2009/042163 | A2 | 4/2009 |
| WO | WO 2009/144008 | A1 | 12/2009 |
| WO | WO 2010/138750 | A2 | 12/2010 |
| WO | WO2012012667 | A2 * | 1/2012 |

OTHER PUBLICATIONS

Beerli, et al., "Engineering Polydactyl Zinc-Finger Transcription Factors," *Nat. Biotechnol.* 20:135-141 (2002).

Bitinaite, et al., "Foki Dimerization Is Required for DNA Cleavage," *Proc. Natl. Acad. Sci.* 95(18): 10,570-10,575 (1998).

Bock, et al., "Reference Maps of Human ES and IPS Cell Variation Enable High-Throughput Characterization of Pluripotent Cell Lines," *Cell* 144(3):439-452 (2011).

Chen, et al., "Bronchiolar Progenitor Cells," *Proc. Am. Thorac. Soc.* 6(7):602-606 (2009).

Cheng, et al., "Defective Intracellular Transport and Processing of CFTR Is the Molecular Basis of Most Cystic Fibrosis," *Cell* 63(4):827-834 (1990).

Choo, et al., "Advances in Zinc Finger Engineering," *Curr. Opin. Struct. Biol.* 10:411-416 (2000).

Coraux, et al., "Embryonic Stem Cells Generate Airway Epithelial Tissue," *Am. J. Respir. Cell Mol. Biol.* 32:87-92 (2005).

Cradick, et al., "ZFN-Site Searches Genomes for Zinc Finger Nuclease Target Sites and Off-Target Sites," *BMC Bioinformatics* 12:152 (2011).

D'Amour, et al., "Efficient Differentiation of Human Embryonic Stem Cells to Definitive Endoderm," *Nat. Biotechnol.* 23(12):1534-1541 (2005).

Engelhardt, et al., "Submucosal Glands Are the Predominant Site of CFTR Expression in the Human Bronchus," *Nature Genetics* 2:240-248 (1992).

Engelhardt, et al., "Expression of the Cystic Fibrosis Gene in Adult Human Lung," *J. Clin. Invest.* 93(2):737-749 (1994).

Hanley, et al., "An Introduction to Induced Pluripotent Stem Cells," *British Journal of Haematology* 151:16-24 (2010).

http://www.uthouston.edu/media/story.htm?id=1930040 news release entitled "Uthealth Stem Cell Scientists Explore Treatments for Blood Disorders and Lung Diseases".

http://www.cfww.org/pub/english/cfwn1/13/288/Stem_Cell_Therapy_for_Cystic_Fibrosis new letter article entitled "Stem Cell Therapy for Cystic Fibrosis?".

http://www.sciencedaily.com/releases/2010/10/101028113612.htm article entitled "Human Induced Pluripotents Stem Cells Generated to Further Treatments for Lung Disease".

http://www.bumc.bu.edu/kottonlab/ article entitled "Induced Pluripotent Stem (IPS) Cells for the Study of Lung Development and Disease".

http://lebao.de/index.php?option=com_content&task=view&id=227<emid=96&lang=en article entitled "Research Project 2 (RP2): Cystic Fibrosis".

http://www.stemcellclinic.com/en/pr/item/1257.html article entitled "Researchers Generate IPSCS to Further Treatments for Lung Disease".

http://www.eurekalert.org/pub_releases/2010-10/bumc-rgi102810.php# press release entitled "Researchers Generate IPSCS to Further Treatments for Lung Disease" (Oct. 28, 2010).

Hung, et al., "Stem Cell-Based Neuroprotective and Neurorestorative Strategies, "*Int. J. Mol. Sci.* 11(5):2039-2055 (2010).

Isalan, et al., "A Rapid, Generally Applicable Method to Engineer Zinc Fingers Illustrated by Targeting the HIV-1 Promoter," *Nat. Biotechnol.* 19(7):656-660 (2001).

Kajstura, et al., "Evidence for Human Lung Stem Cells," *N. Engl. J. Med.* 364(19):1795-1806 (2011).

Kerem, et al., "Identification of the Cystic Fibrosis Gene: Genetic Analysis," *Science* 245(4922):1073-1080 (1989).

Kerem, et al., "Identification of Mutations in Regions Corresponding to the Two Putative Nucleotide (ATP)-Binding Folds of the Cystic Fibrosis Gene," *Proc. Natl. Acad. Sci.* 87(21):8447-8451 (1990).

Kim, et al., "Chimeric Restriction Endonuclease," *Proc. Natl. Acad. Sci.* 91:883-887 (1994).

Kim, et al., "Insertion and Deletion Mutants of Foki Restriction Endonuclease," *J. Biol. Chem.*, 269(50):31,978-31,982 (1994).

Kim, et al., "Hybrid Restriction Enzymes: Zinc Finger Fusions to Fok I Cleavage Domain," *Proc. Natl. Acad. Sci.* 93(3):1156-1160 (1996).

Kreda, et al., "Characterization of Wild-Type and ΔF508 Cystic Fibrosis Transmembrane Regulator in Human Respiratory Epithelia," *Mol. Biol. Cell* 16(5):2154-2167 (2005).

Le, et al., "GFPCRE Fusion Vectors With Enhanced Expression," *Anal Biochem.* 270(2):334-336 (1999).

Li, et al., "Functional Domains in Fok I Restriction Endonuclease," *Proc. Natl. Acad. Sci.* 89:4275-4279 (1992).

Li, et al., "Alteration of the Cleavage Distance of Fok I Restriction Endonuclease by Insertion Mutagenesis," *Proc. Natl. Acad. Sci.* 90:2764-2768 (1993).

Li, et al., "Generation of Rat and Human Induced Pluripotent Stem Cells by Combining Genetic Reprogramming and Chemical Inhibitors," *Cell Stem Cell* 4(1):16-19 (2009).

Lin, et al., "Identification of a Defective Camp-Stimulated Cl-Channel in Cystic Fibrosis Fibroblasts," *J. Biol. Chem.* 262(32):15,345-15,347 (1987).

Lowly, et al., "Generation of Human Induced Pluripotent Stem Cells From Dermal Fibroblasts," *Proc. Natl. Acad. Sci.* 105(8):2883-2888 (2008).

Mueller, et al., "Gene Therapy for Cystic Fibrosis," *Clin. Rev. Allergy Immunol.* 35:164-178 (2008).

Orozco, et al., "Identification of the I507 Deletion by Site-Directed Mutagenesis," *Amer. J. Med. Genetics* 51(2):137-139 (1994).

Ott, et al., "Regeneration and Orthotopic Transplantation of a Bioartificial Lung," *Nature Medicine* 16(8):927-933 (2010).

Pabo, et al., "Design and Selection of Novel CYS2HIS2 Zinc Finger Proteins," *Ann. Rev. Biochem.* 70:313-340 (2001).

Prescott, "The Business of Expoiting Induced Pluripotent Stem Cells," *Phil Trans R Soc B* 366:2323-2328 (2011).

Segal, et al., "Custom DNA-Binding Proteins Come of Age: Polydactyl Zinc-Finger Proteins," *Curr. Opin. Biotechnol.* 12:632-637 (2001).

Somers, et al., "Generation of Transgene-Free Lung Disease-Specific Human Induced Pluripotent Stem Cells Using a Single Excisable Lentiviral Stem Cell Cassette," *Stem Cells* 28(10):1728-1740 (2010).

Van Haute, et al., "Generation of Lung Epithelial-Like Tissue From Human Embryonic Stem Cells," *Respir. Res.* 10:105 (2009).

Warren, et al., "Highly Efficient Reprogramming to Pluripotency and Directed Differentiation of Human Cells With Synthetic Modified MRNA," *Cell Stem Cell* 7(5):618-630 (2010).

West, http://blog.biotimeinc.com/2010/07/es-and-ips-cells-which-holds-future-of.html blog entry entitled "ES and IPS Cells: Which Holds the Future of Biotechnology?".

Wetsel, et al., "Therapeutic Potential of Lung Epithelial Progenitor Cells Derived From Embryonic and Induced Pluripotent Stem Cells," *Annu Rev Med* 62:95-105 (2011).

(56) References Cited

OTHER PUBLICATIONS

Wong, et al., "Gene Therapy, Gene Targeting and Induced Pluripotent Stem Cells: Applications in Monogenic Disease Treatment," *Biotechnology Advances* 28:715-724 (2010).

Yu, et al., "Human Induced Pluripotent Stem Cells Free of Vector and Transgene Sequences," *Science* 324(5928):797-801 (2009).

Kandevelou, et al. "Engineering and Applications of Chimeric Nucleases," Nucleic Acids and Molecular Biology 413-434, XP008071950 (2004).

Lee, et al., "Correction of the ΔF508 Mutation in the Cystic Fibrosis Transmembrane Conductance Regulator Gene by Zinc-Finger Nuclease Homology-Directed Repair," BioResearch Open Access 1(3): 99-108 (2012) doi: 10.1089/biores.2012.0218.

Maeder, et al., "Rapid "Open-Source" Engineering of Customized Zinc-Finger Nucleases for Highly Efficient Gene Modification," Molecular Cell 31: 294-301 (2008).

Urnov, et al. "Highly Efficient Endogenous Human Gene Correction Using Designed Zinc-Finger Nucleases," Nature 435(2): 646-651 (2005) doi: 10.1038/nature03556.

Wong, et al., "Gene Therapy, Gene Targeting and Induced Pluripotent Stem Cells: Applications in Monogenic Disease Treatment," Biotechnology Advances 29(1): 1-10 (2011).

\* cited by examiner

SEQUENCE LISTING

<160> NUMBER OF SEQ ID NOS: 49

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1
aaaatatctt tggtgtttcc                                               20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aaaatatcat tggtgtttcc                                               20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
aaaatatcat tggtgtttcc                                               20

<210> SEQ ID NO 4
<211> LENGTH: 23
<212> TYPE: DNA
<213> ORGANISM: Homo sapiens

<400> SEQUENCE: 4
aaaatatcat ctttggtgtt tcc                                           23

<210> SEQ ID NO 5
<211> LENGTH: 23
<212> TYPE: DNA
<213> ORGANISM: Homo sapiens

<400> SEQUENCE: 5
aaaatatcat ctttggtgtt tcc                                           23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
aaaatatcat tggtgtttcc                                               20

<210> SEQ ID NO 7
<211> LENGTH: 23
<212> TYPE: DNA
<213> ORGANISM: Homo sapiens

<400> SEQUENCE: 7
aaaatatcat ctttggtgtt tcc                                           23

<210> SEQ ID NO 8
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 8

Trp Pro Ser Cys Leu Tyr Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Asn Gly Val Leu Leu Lys Arg
1               5

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Ser Gly Asn Leu Ala Arg
1               5

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Ser Asp Asn Leu Ser Glu
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asn Pro Arg Asn Arg Phe Thr
1               5

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ser Asp Val Leu Ser Glu
1               5
```

```
<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gln Ser Gly His Leu Ser Arg
1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Ser Asp Val Leu Ser Glu
1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Ser Ala Ser Leu Ser Lys
1               5

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gln Asn Ala Thr Arg Ile Asn
1               5

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ser Asp Asn Leu Ser Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 19

Gln Ser Ala Asp Arg Lys Lys
1               5

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Asn Gln Asn Arg Ile Thr
1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Asn Gln Thr Arg Ile Thr
1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Asn Thr Arg Ile Met
1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Thr Ser Gly Asn Leu Thr Arg
1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ser Asn Ala Leu His Gln
1               5
```

```
<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Thr Ser Ser Asp Arg Lys Lys
1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Ser Ser Asp Leu Ser Arg
1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Asp Arg Ser Asn Leu Thr Arg
1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Trp Arg Leu Ser Leu Gln Val
1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gly Ala Asn Leu Ile Lys
1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 30

Arg Ser Asp His Leu Ser Ala
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Glu Ser Arg Tyr Leu Met Val
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asp Arg Ser Asn Arg Lys Thr
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Trp Trp Thr Ser Arg Ala Leu
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

His Ser Asn Ala Arg Lys Thr
1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Thr Leu Gln Asn Arg Met Ser
1               5
```

```
<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Gln Ser Thr Leu Arg Asn
1               5

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
attagaagtg aagtctggaa ataaaacc                                      28

<210> SEQ ID NO 38
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
agtgattatg ggagaactgg atgttcacag tcagtccaca cgtc                    44

<210> SEQ ID NO 39
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
catcatagga aacaccaaag atgatatt                                      28

<210> SEQ ID NO 40
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
atatagatac agaagcgtca tcaaagca                                      28

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
gctttgatga cgcttctgta tctatatt                                      28
```

```
<210> SEQ ID NO 42
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
ccaactagaa gaggtaagaa actatgtg                                             28

<210> SEQ ID NO 43
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cctatgatga atatagatac agaagcgt                                             28

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
acaccaatga tattttcttt aatggtgc                                             28

<210> SEQ ID NO 45
<211> LENGTH: 231
<212> TYPE: DNA
<213> ORGANISM: Homo sapiens
<220> FEATURE:
<221> NAME/KEY: CDS
<222> LOCATION: (23)..(214)

<400> SEQUENCE: 45
taatgatggg ttttatttcc ag act tca ctt cta atg gtg att atg gga gaa      52
                         Thr Ser Leu Leu Met Val Ile Met Gly Glu
                          1               5                  10 ctg gag cct tca gag ggt aaa att aag cac agt gga aga att tca ttc     100
Leu Glu Pro Ser Glu Gly Lys Ile Lys His Ser Gly Arg Ile Ser Phe
                15                  20                  25 tgt tct cag ttt tcc tgg att atg cct ggc acc att aaa gaa aat atc    148
Cys Ser Gln Phe Ser Trp Ile Met Pro Gly Thr Ile Lys Glu Asn Ile
            30                  35                  40 atc ttt ggt gtt tcc tat gat gaa tat aga tac aga agc gtc atc aaa    196
Ile Phe Gly Val Ser Tyr Asp Glu Tyr Arg Tyr Arg Ser Val Ile Lys
        45                  50                  55 gca tgc caa cta gaa gag gtaagaaact atgtgaa                         231
Ala Cys Gln Leu Glu Glu
    60

<210> SEQ ID NO 46
<211> LENGTH: 231
<212> TYPE: DNA
<213> ORGANISM: Homo sapiens
```

```
<400> SEQUENCE: 46
ttcacatagt ttcttacctc ttctagttgg catgctttga tgacgcttct gtatctatat      60
tcatcatagg aaacaccaaa gatgatattt tctttaatgg tgccaggcat aatccaggaa     120
aactgagaac agaatgaaat tcttccactg tgcttaattt taccctctga aggctccagt     180
tctcccataa tcaccattag aagtgaagtc tggaaataaa acccatcatt a              231

<210> SEQ ID NO 47
<211> LENGTH: 64
<212> TYPE: PRT
<213> ORGANISM: Homo sapiens

<400> SEQUENCE: 47

Thr Ser Leu Leu Met Val Ile Met Gly Glu Leu Glu Pro Ser Glu Gly
1               5                   10                  15

Lys Ile Lys His Ser Gly Arg Ile Ser Phe Cys Ser Gln Phe Ser Trp
            20                  25                  30

Ile Met Pro Gly Thr Ile Lys Glu Asn Ile Ile Phe Gly Val Ser Tyr
        35                  40                  45

Asp Glu Tyr Arg Tyr Arg Ser Val Ile Lys Ala Cys Gln Leu Glu Glu
    50                  55                  60

<210> SEQ ID NO 48
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ttatagtaac ca                                                          12

<210> SEQ ID NO 49
<211> LENGTH: 9
<212> TYPE: PRT
<213> ORGANISM: Unknown
<220> FEATURE:
<223> OTHER INFORMATION: Description of Unknown: "LAGLIDADG" family
      peptide motif sequence

<400> SEQUENCE: 49

Leu Ala Gly Leu Ile Asp Ala Asp Gly
1               5
```

METHODS AND COMPOSITIONS FOR ALTERATION OF A CYSTIC FIBROSIS TRANSMEMBRANE CONDUCTANCE REGULATOR (CFTR) GENE

CROSS-REFERENCE TO RELATED APPLICATIONS

The present application claims the benefit of U.S. Provisional Application Nos. 61/511,434 filed Jul. 25, 2011, the disclosure of which is hereby incorporated by reference in its entirety.

TECHNICAL FIELD

The present disclosure is in the fields of genome editing.

BACKGROUND

Lung diseases, including inherited disorders such as Cystic Fibrosis (CF) and Surfactant Protein B (SP-B) Deficiency remain an issue in pediatric populations. SP-B deficiency is a rare lung disease where protein and fat molecules accumulate in the distant parts of the lungs and affect breathing. The disease is caused by a deficiency of the lung surfactant protein B, primarily due to a defect in the SFTPB gene which encodes the pulmonary-associated surfactant B protein (SPB), an amphipathic surfactant protein essential for lung function and homeostasis after birth. The most common mutation in SP-B deficiency is a mutation designated "121ins2" which results in the nucleotide "C" at position 131 being converted into "GAA."

CF is an autosomal recessive disorder affecting 1 in 1500 to 4000 live births, and is one of the most common inherited pediatric disorders. The primary defect in CF is in the regulation of epithelial chloride transport by a chloride channel protein encoded by the cystic fibrosis transmembrane conductance regulator (CFTR) gene. See, e.g., Kerem et al. (1989) *Science* 245:1073-1080; Kreda et al. (2005) *Mol Biol Cell* 16:2154-2167. About 70% of mutations observed in CF patients result from deletion of three base pairs in CFTR's nucleotide sequence, resulting in the loss of the amino acid phenylalanine located at position 508 in the protein (a mutation referred to as ΔF508). In a wild type genome, amino acid 507 is an isoleucine, and is encoded by the codon TAG where the G is nucleotide 1652 in the gene. Amino acid 508 is a phenylalanine, encoded by AAA. In the Δ508 mutation, the G from the 507 codon is deleted along with the first two As of the 508 codon, such that the mutation has the sequence TAA at the deleted 507-508 encoding position. TAA also encodes an isoleucine, but the phenylalanine at wild type position 508 is lost. For the ΔI507 deletion, either the isoleucine at position 506 or 507 is deleted. For this mutation, the nucleotides at 1648-1650 or 1651-1653 are lost, or some combination thereof to result in only one isoleucine in the resultant protein. Compound (heterozygous) mutations (ΔF508 and ΔI507) have also been documented. See, e.g., Orozco et al. (1994) *Am J Med Genet.* 51(2):137-9. CF patients, either compound heterozygous ΔI507/ΔF508 or homozygous ΔF508/ΔF508, fail to express the fully glycosylated CFTR protein and the partially glycosylated protein is not expressed on the cell surface (see, e.g., Kreda et al. (2005) *Mol Biol Cell* 16:2154-2167; Cheng et al. (1990) *Cell* 63:827-834) as is required for CFTR function. Individuals bearing either the ΔI507 or ΔF508 CFTR mutations at only one allele (i.e. wt/ΔI507 or wt/ΔF508) are CF carriers and exhibit no defects in lung cell function. See, e.g., Kerem et al. (1990) *Proc Natl Acad Sci USA* 87:8447-8451.

Although several organ systems are affected by mutations in the CFTR gene, recurrent pulmonary infections are responsible for 80 to 90% of the deaths in CF patients. There is some controversy as to which human lung cell types express CFTR, although recent data indicate that CFTR expression is greatest in the proximal lung, and is predominantly expressed by ciliated cells present in surface airway epithelium. Kreda et al. (2005) *Mol Biol Cell* 16:2154-2167; Engelhardt et al. (1992) *Nat Genet* 2:240-248; Engelhardt et al. (1994) *J Clin Invest* 93:737-749.

Attempts to treat CF via in vivo gene therapy have been hindered by the immunogenic recognition and clearance of the viral vector used to deliver the CFTR transgene, failure to detect long-term expression of CFTR, and likely an inability to achieve stable transduction of relevant stem/progenitor cell populations in the lung Mueller & Flotte (2008) *Clin Rev Allergy Immunol* 35:164-178; Anson et al. (2006) *Curr Gene Ther* 6:161-179. Recently there have been reports of the isolation of human lung stem cells (see Kajstura et al., (2011) *New England Journal of Medicine* 364(19):1795). The authors report that these cells could be isolated, maintained in culture and re-introduced into damaged mouse lungs in vivo, where they were able to structurally integrate into the tissue and reform bronchioles, alveoli and pulmonary vessels.

Thus, there remains a need for the development of novel anti-CF strategies, including treatments and model systems (in vitro such as cell lines and in vivo animal systems) to model and treat CF based on investigation of CFTR mutations and develop stem cells for transplantation and treatment of pulmonary diseases.

SUMMARY

Disclosed herein are methods and compositions for altering a CFTR or SFTPB locus. Also described are models for studying the function of the CF gene (e.g., CFTR) or SFTPB (e.g., SP-B), models for CF and SP-B deficiency drug discovery and for treating CF or SP-B as well as methods of making and using these model systems. The compositions and methods described herein can be used for genome editing of CFTR or SFTPB, including, but not limited to: cleaving of a CFTR or SFTPB gene in an animal cell resulting in targeted alteration (insertion, deletion and/or substitution mutations) in the CFTR or SFTPB gene, including the incorporation of these targeted alterations into the germline; targeted introduction into a CFTR or a SFTPB gene of non-endogenous nucleic acid sequences, the partial or complete inactivation of a CFTR gene in an animal; correction of an SFTPB gene in an animal; methods of inducing homology-directed repair at a CFTR or SFTPB locus; generation of a pulmonary stem cell population with a corrected CFTR or SFTPB gene for transplant into a patient in need thereof, and generation of transgenic animals modified at a CFTR and/or SFTPB locus (e.g., rodents and non-human primates).

In one aspect, described herein is a zinc-finger protein (ZFP) that binds to target site in a CFTR gene in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a CFTR gene. In some embodiments, the zinc finger domain recognizes a target site in a mutated CFTR gene such that the ZFN pair will cleave only a mutated CFTR allele.

In one aspect, described herein is a zinc-finger protein (ZFP) that binds to target site in a SFTPB gene in a genome, wherein the ZFP comprises one or more engineered zinc-finger binding domains. In one embodiment, the ZFP is a zinc-finger nuclease (ZFN) that cleaves a target genomic region of interest, wherein the ZFN comprises one or more engineered zinc-finger binding domains and a nuclease cleavage domain or cleavage half-domain. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). In certain embodiments, the zinc finger domain recognizes a target site in a SFTPB gene.

The ZFN may bind to and/or cleave a CFTR or SFTPB gene within the coding region of the gene or in a non-coding sequence within or adjacent to the gene, such as, for example, a leader sequence, trailer sequence or intron, or within a non-transcribed region, either upstream or downstream of the coding region.

In another aspect, described herein is a TALE protein (Transcription activator like) that binds to target site in a CFTR or SFTPB gene in a genome, wherein the TALE comprises one or more engineered TALE DNA binding domains. In one embodiment, the TALE is a nuclease (TALEN) that cleaves a target genomic region of interest, wherein the TALEN comprises one or more engineered TALE DNA binding domains and a nuclease cleavage domain or cleavage half-domain Cleavage domains and cleavage half domains can be obtained, for example, from various restriction endonucleases and/or homing endonucleases. In one embodiment, the cleavage half-domains are derived from a Type IIS restriction endonuclease (e.g. Fok I). In certain embodiments, the TALE DNA binding domain recognizes a target site in a CFTR or SFTPB gene.

The TALEN may bind to and/or cleave a CFTR or SFTPB gene within the coding region of the gene or in a non-coding sequence within or adjacent to the gene, such as, for example, a leader sequence, trailer sequence or intron, or within a non-transcribed region, either upstream or downstream of the coding region. In certain embodiments, the TALE DNA binding domain recognizes a target site in a CFTR gene. In some embodiments, the TALE DNA binding domain recognizes a target site in a mutated CFTR gene such that the TALEN pair will cleave only a mutated CFTR allele.

In another aspect, described herein are compositions comprising one or more of the zinc-finger or TALE nucleases described herein. In certain embodiments, the composition comprises one or more zinc-finger or TALE nucleases in combination with a pharmaceutically acceptable excipient.

In another aspect, described herein is a polynucleotide encoding one or more ZFNs or TALENs described herein. The polynucleotide may be, for example, mRNA.

In another aspect, described herein is a ZFN or TALEN expression vector comprising a polynucleotide, encoding one or more ZFNs or TALENs described herein, operably linked to a promoter.

In another aspect, described herein is a host cell comprising one or more ZFN or TALEN expression vectors. The host cell may be stably transformed or transiently transfected or a combination thereof with one or more ZFP or TALEN expression vectors. In one embodiment, the host cell is an embryonic stem cell. In one embodiment, the host cell is a lung stem cell. In other embodiments, the one or more ZFP or TALEN expression vectors express one or more ZFNs or TALENs in the host cell. In another embodiment, the host cell may further comprise an exogenous polynucleotide donor sequence. In any of the embodiments, described herein, the host cell can be in an embryo, for example a one or more mouse, rat, rabbit or other mammal embryos (e.g., a non-human primate).

In another aspect, described herein is a method for cleaving one or more CFTR or SFTPB genes in a cell, the method comprising: (a) introducing, into the cell, one or more polynucleotides encoding one or more ZFNs or TALENs that bind to a target site in the one or more genes under conditions such that the ZFN(s) is (are) or TALENs is (are) expressed and the one or more genes (CFTR and/or SFTPB) are cleaved.

In another embodiment, described herein is a method for modifying one or more CFTR or SFTPB gene sequence(s) in the genome of a cell, the method comprising (a) providing a cell comprising one or more CFTR or SFTPB sequences; and (b) expressing first and second zinc-finger nucleases (ZFNs) or TALENs in the cell, wherein the first ZFN or TALEN cleaves at a first cleavage site and the second ZFN or TALEN cleaves at a second cleavage site, wherein the gene sequence is located between the first cleavage site and the second cleavage site, wherein cleavage of the first and second cleavage sites results in modification of the gene sequence by non-homologous end joining and/or homology directed repair. Optionally, the cleavage results in insertion of an exogenous sequence (transgene) also introduced into the cell. In other embodiments, non-homologous end joining results in a deletion between the first and second cleavage sites. The size of the deletion in the gene sequence is determined by the distance between the first and second cleavage sites. Accordingly, deletions of any size, in any genomic region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein. Using these methods and compositions, mutant CFTR and/or SFTPB proteins may be developed that lack one or more of the known domains. These constructs can then be used to study the function of the protein within a cell.

In another aspect, specific mutations associated with CFTR or SFTPB can be corrected to understand the function of the gene that harbors the mutation, and/or to discover phenotypes associated with the correction of the mutant gene, including, for example, mutations ΔF508 and/or ΔI507 in CFTR. Such an understanding then can be used to design cells, cell lines and transgenic animals for use in drug screening and drug discovery, for example for treatments of CF or SP-B deficiency.

In another aspect, site specific mutations in CFTR or SFTPB can be constructed to model known or novel mutations. For example, the ΔF508 mutation in CFTR can be constructed in a cell, cell line, primary cell or transgenic animal. In one embodiment, a cell, cell line or transgenic animal carrying a heterozygous genotype for CFTR is constructed, while in another embodiment, a homozygous cell, cell line or transgenic animal is made carrying two mutant copies in both alleles of a desired locus.

In another aspect, described herein are methods of inactivating a CFTR or SFTPB gene in a cell by introducing one or more proteins, polynucleotides and/or vectors into the cell as described herein. In any of the methods described herein the ZFNs or TALENs may induce targeted mutagenesis, targeted deletions of cellular DNA sequences, and/or facilitate targeted recombination at a predetermined chromosomal locus. Thus, in certain embodiments, the ZFNs or TALENs delete or insert one or more nucleotides of the target gene. In some embodiments, the CFTR or SFTPB gene is inactivated by ZFN or TALEN cleavage followed by non-homologous end joining (NHEJ). In other embodiments, a genomic sequence in the target gene is replaced, for example using a ZFN or TALEN (or vector encoding said ZFN or TALEN) as described herein and a "donor" sequence that is inserted into the gene following targeted cleavage with the ZFN or TALEN. The donor sequence may be present in the ZFN or TALEN vector, present in a separate vector (e.g., Ad or LV vector) or, alternatively, may be introduced into the cell using a different nucleic acid delivery mechanism. In one aspect, the donor sequence causes a known mutation, e.g., the ΔF508 mutation in the CFTR protein. In certain embodiments, the donor sequence includes a sequence that, following targeted integration of the donor sequence into a ΔF508 mutant allele, results in a base pair substitution (A>G) in intron 9 of CFTR (note, A>G substitution occurs at position −61 in intron 9 with respect to start of exon 10: i.e. −61A>G).

In another aspect, described herein are methods of correcting a CFTR or SFTPB gene (e.g., a mutant gene) in a cell by introducing one or more proteins, polynucleotides and/or vectors into the cell as described herein. In any of the methods described herein the ZFNs or TALENs may induce targeted mutagenesis, targeted deletions of cellular DNA sequences, and/or facilitate targeted recombination at a predetermined chromosomal locus. Thus, in certain embodiments, the ZFNs or TALENs delete or insert one or more nucleotides of or into the target gene. In some embodiments the CFTR and/or SFTPB gene is corrected by ZFN or TALEN cleavage followed by non-homologous end joining (NHEJ). In other embodiments, a genomic sequence in the target gene is replaced, for example using a ZFN or TALEN (or vector encoding said ZFN or TALEN) as described herein and a "donor" sequence that is integrated into the gene following targeted cleavage with the ZFN or TALEN correcting the sequence of the CFTR or SFTPB gene. In some embodiments, the donor sequence is inserted into a safe harbor locus (see co-owned United States Patent publication 20080299580). The donor sequence may be present in the ZFN or TALEN vector, present in a separate vector (e.g., Ad or LV vector) or, alternatively, may be introduced into the cell using a different nucleic acid delivery mechanism. In one aspect, the donor sequence corrects a known mutation, for example correction of the ΔF508 mutation. In any of the embodiments described herein, the correction results in expression of a CFTR protein that is fully glycosylated.

In any of the methods or compositions described herein, the cell containing the CFTR or SFTPB locus can be a stem cell. Specific stem cell types that may be used with the methods and compositions of the invention include embryonic stem cells (ESC), hematopoietic stem cells, nerve stem cells, skin stem cells, muscle stem cells, lung stem cells and induced pluripotent stem cells (iPSC). The iPSCs can be derived from patient samples or from normal donors wherein the patient derived iPSC can be mutated to normal gene sequence at the gene of interest, or normal cells can be altered to the known disease allele at the gene of interest. Panels of these iPSC can be used to create isogenic cells with both patient and normal cells carrying one or more mutations at their endogenous CFTR or SFTPB loci. These cells can be used to create cell lines and/or transgenic animals differing only at the mutations of interest to study multigene effects of disease severity and possible therapeutic treatments for CF and/or SB-P deficiency. Other cell types that may be used for these studies are patient derived fibroblasts or patient derived stem cells. In another aspect, the invention provides methods and compositions for the development of lung (or other) stem cells for transplant into patients in need thereof. The lung stem cells for transplant may be derived from the patient, corrected at the disease associated site in the CFTR or SFTPB locus and reintroduced into a patient. In other aspects the lung stem cells may be from a universal source and contain a wild type CFTR or SFTPB gene, where the HLA and/or other self-markers have been altered (see co-owned United States Patent Publication No. 20120060230) such that the transplanted cells are not rejected by the patient.

In another aspect, described herein is a method of creating one or more heritable mutant alleles in at least one CFTR or SFTPB locus of interest, the method comprising modifying one or more CFTR or SFTPB loci in the genome of one or more cells of an animal embryo by any of the methods described herein; raising the embryo to sexual maturity; and allowing the sexually mature animal to produce offspring; wherein at least some of the offspring comprise the mutant alleles. In certain embodiments, the animal is a small mammal, for example a rabbit or a rodent such as rat, a mouse or a guinea pig. In other embodiments, the animal is a non-human primate.

In any of the methods described herein, the polynucleotide encoding the zinc finger nuclease(s) or TALEN(s) can comprise DNA, RNA or combinations thereof. In certain embodiments, the polynucleotide comprises a plasmid. In other embodiments, the polynucleotide encoding the nuclease comprises mRNA.

In a still further aspect, provided herein is a method for site specific integration of a nucleic acid sequence into a CFTR or SFTPB locus of a chromosome. In certain embodiments, the method comprises: (a) injecting an embryo with (i) at least one DNA vector, wherein the DNA vector comprises an upstream sequence and a downstream sequence flanking the nucleic acid sequence to be integrated, and (ii) at least one RNA molecule encoding a zinc finger or TALE nuclease that recognizes the site of integration in the CFTR or SFTPB locus, and (b) culturing the embryo to allow expression of the zinc finger or TALE nuclease, wherein a double stranded break introduced into the site of integration by the zinc finger nuclease or TALEN is repaired, via homologous recombination with the DNA vector, so as to integrate the nucleic acid sequence into the chromosome.

Suitable embryos may be derived from several different vertebrate species, including mammalian, bird, reptile, amphibian, and fish species. Generally speaking, a suitable embryo is an embryo that may be collected, injected, and cultured to allow the expression of a zinc finger or TALE nuclease. In some embodiments, suitable embryos may include embryos from small mammals (e.g., rodents, rabbits, etc.), companion animals, livestock, or primates. Non-limiting examples of rodents may include mice, rats, hamsters, gerbils, and guinea pigs. Non-limiting examples of companion animals may include cats, dogs, rabbits, hedgehogs, and ferrets. Non-limiting examples of livestock may include horses, goats, sheep, swine, llamas, alpacas, and cattle. Non-limiting examples of primates may include capuchin monkeys, chimpanzees, lemurs, macaques, marmosets, tamarins, spider monkeys, squirrel monkeys, and vervet monkeys. In other embodiments, suitable embryos may include embryos from fish, reptiles, amphibians, or birds. Alternatively, suitable embryos may be insect embryos, for instance, a Drosophila embryo or a mosquito embryo.

Also provided is an embryo comprising at least one DNA vector, wherein the DNA vector comprises an upstream sequence and a downstream sequence flanking the nucleic acid sequence to be integrated, and at least one RNA molecule encoding a zinc finger nuclease that recognizes the chromosomal site of integration. Organisms derived from any of the embryos as described herein are also provided.

In another aspect provided by the methods and compositions of the invention is the use of cells, cell lines and animals (e.g., transgenic animals) in the screening of drug libraries and/or other therapeutic compositions (i.e., antibodies, structural RNAs, etc.) for use in treatment of an animal afflicted with CF or SB-P deficiency. Such screens can begin at the cellular level with manipulated cell lines or primary cells, and can progress up to the level of treatment of a whole animal (e.g., human).

A kit, comprising the ZFPs or TALENs of the invention, is also provided. The kit may comprise nucleic acids encoding the ZFPs or TALENs, (e.g. RNA molecules or ZFP or TALEN encoding genes contained in a suitable expression vector), or aliquots of the ZFP or TALEN proteins, donor molecules, suitable host cell lines, instructions for performing the methods of the invention, and the like.

These and other aspects will be readily apparent to the skilled artisan in light of this disclosure as a whole.

BRIEF DESCRIPTION OF THE DRAWINGS

FIG. 2A is a schematic depicting the targeted allele. Shown are the primers 1/1' utilized for upstream characterization (yielding a 1.8 kb amplicon) and primers 2/2' utilized for downstream characterization (yielding a 0.9 kb amplicon). FIG. 2B is a gel depicting identification of an upstream 1.8 kb 1/1' amplicon in 18 of 21 CFTR-targeted iPSC clones. iPSC clone numbers are shown above the individual lanes. As shown, no 1.8 kb amplicon was identified for other puroR iPS clones (clones 17-22, 17-23), for the original CF clone 17 iPSC, nor for MEFs.

FIG. 3A is a gel showing RT-PCR analysis of CFTR expression for the seven CFTR targeted CF iPS clones. Also shown is CFTR expression by the original Clone 17 CF ΔI507/ΔF508 iPS cells, WA09 (H9) hES cells, and the A549 lung epithelial cell line. The expected size of PCR amplified cDNA (exons 8/9 to 11) is 0.46 kb. Analysis of clones 17-1, 17-9, 17-14, and 17-16 yielded the expected band (indicated on the Figure), whereas clones 17-13, 17-17, and 17-20 also exhibited a larger size band. FIG. 3B shows the sequence of CFTR RT-PCR product from original ΔI507/ΔF508 CFTR iPS cells (Clone 17, top strand showing ΔI507 (SEQ ID NO:1) and bottom strand showing ΔF508 (SEQ ID NO:2)); corrected wt/ΔF508 CFTR iPS cells (Clone 17-1, top stand showing ΔF508 (SEQ ID NO:3), bottom strand showing wild type (wt) (SEQ ID NO:4)), and wt/wt CFTR A549 cells (SEQ ID NO:5).

FIG. 4, panels A and B, depict Cre-mediated excision of puroTK cassette from corrected CF wt/ΔF508 iPS cells.

FIG. 5A shows gene expression patterns of original Clone 17 CF iPSC, either undifferentiated (d0) or following culture in Activin A for 1-3 days showing clear up-regulation of both Sox17 and. CFTR mRNAs over time. FIG. 5B shows gene expression pattern of corrected, Cre-excised Clone 17-9-C1 iPSC and also demonstrates up-regulation of both Sox17 and CFTR mRNA by days 3-5 of culture in Activin A. FIG. 5C shows gene expression levels in the indicated clones and cells.

FIG. 6A shows an illustration of the CFTR gene sequence showing the binding sites for each of the ZFNs (SEQ ID NO:45 corresponds to the top DNA strand, SEQ ID NO:46 is bottom DNA strand; SEQ ID NO:47 shows the amino acid sequence; SEQ ID NO:48 shows a portion of the gene sequence corresponding to the mutation, which is underlined in the Figure (TTATAGTAACCA)). The ZFNs bind sequences within Exon1 of CFTR. Additionally, a box is placed around the region where the Δ508 mutation can arise. FIG. 6B depicts gels demonstrating ZFN-mediated genome modification in K562 cells. The 32365/32366 and 32375/32376 ZFN pairs caused a 9% and 12% rate of indel formation, respectively.

DETAILED DESCRIPTION

Figure 1:
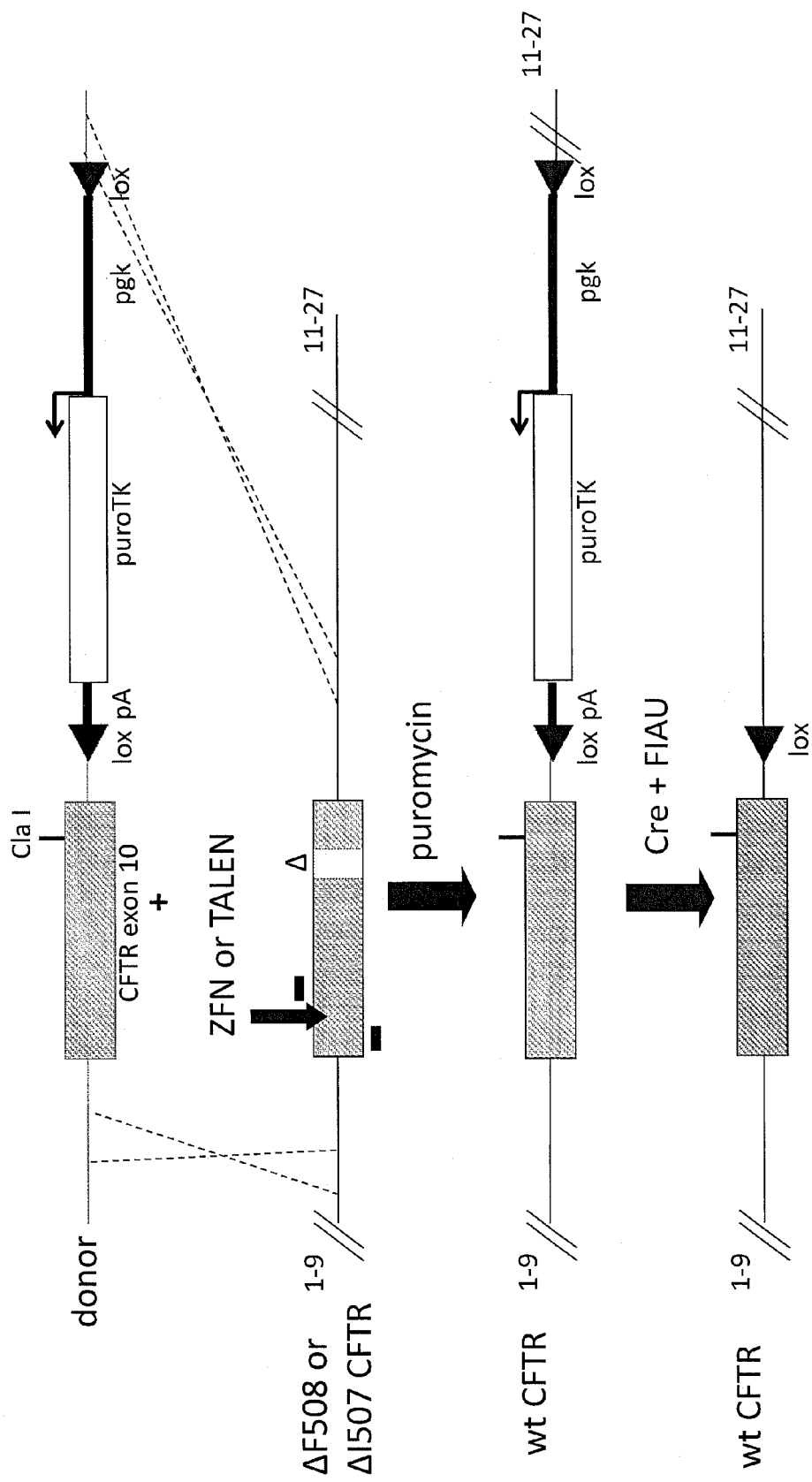
FIG. 1 is a schematic depicting targeted, ZFN or TALEN-mediated correction of ΔI507 or ΔF508 CFTR mutations in the genomes of CF patient derived induced pluripotent stem cells (CF iPSC) and showing co-delivery of CFTR-specific nuclease together with CFTR donor, followed by Cre-recombinase mediated excision. lox: lox P sites; pgk: murine phosphoglycerate kinase promoter; puroTK: puromycin-thymidine kinase fusion gene; pA: polyadenylation signal sequences; Cre: Cre-recombinase.

Disclosed herein are compositions and methods for treating and/or developing models useful in evaluating treatment of CF or SB-P deficiency. In particular, nuclease-mediated cleavage and integration is used to create or repair known mutations in the CFTR or SFTPB gene. These compositions and methods can be used to correct or create specific CFTR or SFTPB mutations in any selected genetic background to allow for study of CF or SB-P deficiency.

Thus, the methods and compositions described herein can be used to create isogenic panels of a set of mutations in CFTR or SFTPB to allow for controlled study of these mutations, to investigate the link between a certain mutation and cellular dysfunction and to identify phenotypes associated with the mutation or with the correction of the mutation. In addition, any CFTR or SFTPB mutation can be introduced into patient derived cells, e.g. patient derived induced pluripotent stem cells (iPSCs), to investigate the effects of a certain mutation in a patient cell background. In addition, creation of CFTR or SFTPB mutants with in-frame alterations is also part of the invention described herein, to allow for fine-tuned analysis of the functional domains of these proteins. Furthermore, CFTR or SFTPB mutations associated with CF or SB-P2 can be created within the native gene in model animals (rat, non-human primate, etc.) to generate CF or SB-P deficiency models. These animals may contain one or more inserted CFTR and/or SFTPB mutations.

Also described herein are methods and compositions for altering specific CFTR or SFTPB defects in patient cells. For example, mutated CFTR or SFTPB genes may be knocked out by use of specific nucleases that will only act on mutant alleles and not act on a wild type gene sequence. Knock out of a specific gene may be a result of cleavage followed by NHEJ, or by cleavage at two loci within the gene to delete a large portion of the gene, or by cleavage followed by targeted integration of an oligonucleotide or larger donor DNA. Additionally, described herein are methods and compositions to correct specific mutations in CFTR or SFTPB associated genes in patient cells. Such corrected cells may then be re-introduced back to the patient for treatment of CF or SF-B deficiency. Patient cells may be stem cells or iPSC. Universal stem cells may also be created using the methods of the invention which then may be used to treat any CF or SF-B patient.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolfe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein.

Zinc finger binding domains can be "engineered" to bind to a predetermined nucleotide sequence, for example via engineering (altering one or more amino acids) of the recognition helix region of a naturally occurring zinc finger protein. Similarly, TALEs can be "engineered" to bind to a predetermined nucleotide sequence, for example by engineering of the amino acids involved in DNA binding (the RVD region). Therefore, engineered zinc finger proteins or TALE proteins are proteins that are non-naturally occurring. Non-limiting examples of methods for engineering zinc finger proteins and TALEs are design and selection. A designed protein is a protein not occurring in nature whose design/composition results principally from rational criteria. Rational criteria for design include application of substitution rules and computerized algorithms for processing information in a database storing information of existing ZFP or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein or TALE is a protein not found in nature whose production results primarily from an empirical process such as phage display, interaction trap or hybrid selection. See e.g., U.S. Pat. No. 5,789,538; U.S. Pat. No. 5,925,523; U.S. Pat. No. 6,007,988; U.S. Pat. No. 6,013,453; U.S. Pat. No. 6,200,759; WO 95/19431; WO 96/06166; WO 98/53057; WO 98/54311; WO 00/27878; WO 01/60970 WO 01/88197 and WO 02/099084.

"Recombination" refers to a process of exchange of genetic information between two polynucleotides. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger or TALEN proteins can be used for additional double-stranded cleavage of additional target sites within the cell.

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the first nucleotide sequence (the "donor sequence") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

Any of the methods described herein can be used for partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or non-coding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain) See, also, U.S. Patent Publication Nos. 2005/0064474, 20070218528 and 2008/0131962, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the Bonn of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogenous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, random mutation) can be used to modulate expression. Gene inactivation refers to any reduction in gene expression as compared to a cell that does not include a ZFP or TALEN as described herein. Thus, gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP or TALE DNA-binding domain is fused to an activation domain, the ZFP or TALE DNA-binding domain and the activation domain are in operative linkage if, in the fusion polypeptide, the ZFP or TALE DNA-binding domain portion is able to bind its target site and/or its binding site, while the activation domain is able to up-regulate gene expression. When a fusion polypeptide in which a ZFP or TALE DNA-binding domain is fused to a cleavage domain, the ZFP or TALE DNA-binding domain and the cleavage domain are in operative linkage if, in the fusion polypeptide, the ZFP or TALE DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolatereductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

Nucleases

Described herein are compositions, particularly nucleases, which are useful in correction of one or more mutant CFTR alleles and/or mutation of one or more CFTR alleles, for example to generate models of CF. In certain embodiments, the nuclease is naturally occurring. In other embodiments, the nuclease is non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector nucleases; meganuclease DNA-binding domains with heterologous cleavage domains).

A. DNA-Binding Domains

In certain embodiments, the nuclease is a meganuclease (homing endonuclease). Naturally-occurring meganucleases recognize 15-40 base-pair cleavage sites and are commonly grouped into four families: the LAGLIDADG (SEQ ID NO: 49) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII. Their recognition sequences are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) Nucleic Acids Res. 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue.

In certain embodiments, the nuclease comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. No. 5,420,032; U.S. Pat. No. 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol. Biol.* 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like effectors (TALE) which mimic plant transcriptional activators and manipulate the plant transcriptome (see Kay et al (2007) *Science* 318:648-651). These proteins contain a DNA binding domain and a transcriptional activation domain. One of the most well characterized TALEs is AvrBs3 from Xanthomonascampestgris pv. Vesicatoria (see Bonas et al (1989) *Mol Gen Genet* 218: 127-136 and WO2010079430). TALEs contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al (2006) *J Plant Physiol* 163(3):256-272). In addition, in the phytopathogenic bacteria Ralstoniasolanacearum two genes, designated brg11 and hpx17 have been found that are homologous to the AvrBs3 family of *Xanthomonas* in the *R. solanacearumbiovar* 1 strain GMI1000 and in the biovar 4 strain RS1000 (See Heuer et al (2007) *Appl and Envir Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*.

Thus, in some embodiments, the DNA binding domain that binds to a target site a CFTR gene is an engineered domain from a TAL effector similar to those derived from the plant pathogens *Xanthomonas* (see Boch et al, (2009) *Science* 326: 1509-1512 and Moscou and Bogdanove, (2009) *Science*326: 1501) and Ralstonia (see Heuer et al (2007) *Applied and Environmental Microbiology* 73(13): 4379-4384); U.S. Patent Publication Nos. 20110301073 and 20110145940.

In certain embodiments, the DNA binding domain that binds to a target site a CFTR gene comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

In addition, as disclosed in these and other references, DNA domains (e.g., multi-fingered zinc finger proteins) may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The zinc finger proteins described herein may include any combination of suitable linkers between the individual zinc fingers of the protein. In addition, enhancement of binding specificity for zinc finger binding domains has been described, for example, in co-owned WO 02/077227.

Selection of target sites; DNA-binding domains and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Nat'l Acad Sci USA* 93(3):1156-1160. More recently, ZFNs have been used for genome modification in a variety of organisms. See, for example, United States Patent Publications 20030232410; 20050208489; 20050026157; 20050064474; 20060188987; 20060063231; and International Publication WO 07/014,275.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a DNA binding domain and two Fok I cleavage half-domains can also be used.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in International Publication WO 07/014,275, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474; 20060188987 and 20080131962, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the Fold cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See, e.g., U.S. Patent Publication No. 2008/0131962, the disclosure of which is incorporated by reference in its entirety for all purposes.

In certain embodiments, the engineered cleavage half-domain comprises mutations at positions 486, 499 and 496 (numbered relative to wild-type FokI), for instance mutations that replace the wild type Gln (Q) residue at position 486 with a Glu (E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). (See US Patent Publication No. 20110201055).

Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in WO 2009/042163 and U.S. Publication No. 20090068164. Nuclease expression constructs can be readily designed using methods known in the art. See, e.g., United States Patent Publications 20030232410; 20050208489; 20050026157; 20050064474; 20060188987; 20060063231; and International Publication WO 07/014,275. Expression of the nuclease may be under the control of a constitutive promoter or an inducible promoter, for example the galactokinase promoter which is activated (de-repressed) in the presence of raffinose and/or galactose and repressed in presence of glucose.

Target Sites

As described in detail above, DNA domains can be engineered to bind to any sequence of choice in a CFTR locus or in a SFTPB locus. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual (e.g., zinc finger) amino acid sequences, in which each triplet or quadruplet nucleotide sequence is associated with one or more amino acid sequences of DNA binding domain which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Patent Publication No. 20110301073.

Exemplary selection methods applicable to DNA-binding domains, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Patent Publication No. 20110287512.

Donors

As noted above, alteration of a CFTR or SFTPB gene can include insertion of an exogenous sequence (also called a "donor sequence" or "donor"), for example for correction of a mutant gene or for mutation of wild-type gene. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded or double-stranded and can be introduced into a cell in linear or circular form. See, e.g., U.S. Pat. No. 7,888,121 and U.S. Patent Publication Nos. 2009/0263900; 20100047805 and 20110207221, incorporated by reference herein. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the CFTR gene. However, it will be apparent that the donor may comprise a promoter and/or enhancer, for example a constitutive promoter or an inducible or tissue specific promoter.

Furthermore, although not required for expression, exogenous sequences may also be transcriptional or translational regulatory sequences, for example, promoters, enhancers, insulators, internal ribosome entry sites, sequences encoding 2A peptides and/or polyadenylation signals.

Delivery

The nucleases, polynucleotides encoding these nucleases, donor polynucleotides and compositions comprising the proteins and/or polynucleotides described herein may be delivered in vivo or ex vivo by any suitable means.

Methods of delivering nucleases as described herein are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the zinc finger or TALEN protein(s). Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors. When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson *Science* 256:808-813 (1992); Nabel&Felgner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer &Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by AmaxaBiosystems (Cologne, Germany), Maxcyte, Inc. (Rockville, Md.), BTX Molecular Delivery Systems (Holliston, Mass.) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamiid et al (2009) *Nature Biotechnology* 27(7):643).

The use of RNA or DNA viral based systems for the delivery of nucleic acids encoding engineered ZFPs take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hetnionat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al, *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al. *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV3, AAV4, AAV5, AAV6, AAV8, AAV9, and AAVrh10 can also be used in accordance with the present invention. Additionally, pseudotyped AAV vectors may be used wherein the AAV vector ITRs and the AAV capsid proteins are from different AAV serotypes, or chimeric AAV particles where the capsid proteins are made from more than one AAV serotype.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for anti-tumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route. In particular, for delivery to pulmonary tissues, introduction of vectors may be done using the bronchial artery. Bronchial delivery may occur in conjunction with stop flow techniques, or with the use of endothelial barrier disrupters (e.g. VEGF or histamine) to increase uptake.

Vectors suitable for introduction of polynucleotides described herein include non-integrating lentivirus vectors (IDLV). See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222; U.S. Patent Publication No 2009/0054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, a donor polynucleotide can be carried by a plasmid, while the one or more nucleases can be carried by a AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

Applications

The instant invention describes methods and compositions that can be used to introduce or repair mutations in lung disorders such as CF disease and/or SB-P deficiency. In particular, specific mutations at the CFTR gene that have been shown to be pathogenic in the development of CF include ΔF508 and ΔI507. Mutations in SFTPB are the most common mutations leading to SB-P deficiency and include: 121ins2 (121C>GAA). Thus, the methods and compositions of the instant invention are useful for repairing (correcting) mutations in CFTR and/or SB-P either by repair of patient derived stem cells or by in vivo administration of nucleases and donor molecule. Also useful described herein are methods for developing cell and transgenic animal models to study the intracellular pathology associated with CFTR and SFTPB mutations and for studying the consequences of these mutations within the whole organism. As such, tools designed to knock out, knock in and/or correct specific CFTR or SFTPB mutations (for example the ΔF508 mutation in CFTR) can be used to create cell and animal models useful in furthering an understanding of the underlying biology and in the development of specific drug therapies. Further, specific nucleases targeted to a specific CFTR or SFTPB mutation can be employed to knock out or correct the mutation. Nucleases can also be used to cause the insertion of a CFTR or SFTPB mutation-specific tag in order to develop cell lines for the investigation of CFTR or SFTPB mutation specific therapeutics.

Additionally, cells, cell lines and transgenic animals as described herein are useful for drug development. Such cells and animals may reveal phenotypes associated with a particular mutation (e.g. CFTR ΔF508) or with its correction, and may be used to screen drugs that will interact either specifically with the mutation(s) in question, or that are useful for treatment of the disease in an afflicted animal. Therapeutically, iPSCs can be derived ex vivo from a patient afflicted with a known genetic mutation associated with CF or SB-P deficiency, and the mutation can be corrected using ZFN- or TALEN-mediated gene correction. Similarly, lung, skin or other stem cells may be isolated from a patient and then corrected at the CFTR or SFTPB locus using the methods and compositions of the invention. The corrected stem cells can then be used to treat the patient. In addition, cell lines can be made from patient samples containing the CFTR or SFTPB mutations of interest. These cell lines can provide tools to investigate the effects of specific mutations in patient-specific iPS cell lines. For example, parallel cell lines can be generated in which one line is corrected at the mutation of interest while its parallel line is not. This creates cell lines that are only different by the disease-causing mutation. The resulting isogenic panel of iPSCs that carry different allelic forms of CFTR or SFTPB at the endogenous locus provides a genetic tool for repair of disease-specific mutations, drug screening and discovery, and disease mechanism research.

The availability of patient-specific iPS cell lines with both repaired and induced mutations and their isogenic controls are also useful in a wide-variety of medical applications, including but not limited to, the study of mechanisms by which these mutations cause disease and translating "laboratory cures" to treatments for patients who actually manifest disease induced by these mutations. In addition, the lines may be useful in screening potential therapeutic compounds to identify those compounds that exhibit highly specific behavior.

Cellular transplantation of lung stem/progenitor cells represents a potential therapeutic approach for a variety of inherited monogenic lung diseases such as CF or SB-P deficiency. Corrected CF or SB-P iPS cells present a potential source of patient-specific cells capable, in vitro, of differentiation into various lung stem/progenitor cells (see, e.g., Chen et al. (2009) *Proc Am Thorac Soc* 6:602-606; Kajstura et al. (2011) *N Engl J Med* 364:1795-1806; either for transplantation of autologous lung cells or for seeding de-vitalized lung scaffolds ex vivo to generate autologous lungs (see, e.g., Ott et al. (2010) *Nat Med* 16:927-933). In addition, there are reports (see Kajstura et al, ibid) that human lung stem cells have been identified which are capable of forming bronchioles, aveoli, and pulmonary vessels when given to mice with damaged lungs in vivo. Thus there is a potential that lung or other types of stem cells may be able to be isolated from patients, modified by ZFNs or TALENs ex vivo, and then reintroduced to the patient, thus treating the disease. Thus, the methods and compositions described herein can be used to generate cells (and their progeny) for use in transplantation that are corrected (both genotypically and phenotypically) for the CF or SB-P deficiency disease-causing mutation. These transplanted cells would not elicit an immune response in the recipient. Using skin or blood cells from affected patients, autologous induced pluripotent stem (iPS) cells are derived. Utilizing site-specific homology-directed repair, the disease-causing mutation would then be corrected in the endogenous, chromosomal DNA sequence Finally, a directed differentiation approach would be employed to obtain highly purified populations of the relevant lung stem/progenitor cells from the corrected iPS cells for purposes of transplantation.

The following Examples relate to exemplary embodiments of the present disclosure in which the nuclease comprises a zinc finger nuclease (ZFN) or a TALEN. It will be appreciated that this is for purposes of exemplification only and that other nucleases can be used, for instance homing endonucleases (meganucleases) with engineered DNA-binding domains and/or fusions of naturally occurring of engineered homing endonucleases (meganucleases)

EXAMPLES

Example 1

Materials and Methods

A. Cystic Fibrosis Primary Fibroblasts

CF primary fibroblast line GM04320 was obtained (Coriell Repository, Camden, N.J.) from a patient (17 year old male) reported homozygous for the ΔF508 mutation. Clinical symptoms for this patient were reported as advanced pulmonary disease and pancreatic insufficiency; in addition, defective cAMP stimulated chloride channel activity was demonstrated in fibroblasts from this patient. See, also, Lin & Gruenstein (1987) *J Biol Chem* 262:15345-15347.

Sequencing of the CFTR alleles in genomic DNA isolated from the GM04320 fibroblasts demonstrated that the patient was, in fact, a compound heterozygote with one allele being ΔF508 and the other ΔI507. ΔF508/ΔI507 compound heterozygosity has previously been reported in CF patients. See, e.g., Kerem et al. (1990) *Proc Natl Acad Sci USA* 87:8447-8451.

B. CF iPS Cell Generation and Characterization

The pMXs retroviral vectors encoding human reprogramming factors (OCT4 [17964], SOX2 [17965], KLF4 [17967], C-MYC [17966], NANOG [18115]) as described in Lowry et al. (2008) *Proc Natl Acad Sci USA* 105:2883-2888 were introduced into the CF primary fibroblasts. Non-integrating methods or integration-free methods (e.g. RNA, episomal vectors, excisable reprogramming transgenes, and/or small molecules) can also be employed for introducing of reprogramming factors. See, e.g., Somers et al. (2010) *Stem Cells* 28:1728-1740; Warren et al. (2010) *Cell Stem Cell* 7:618-630; Yu et al. (2009) *Science* 324:797-801; Li et al. (2009) *Cell Stem Cell* 4:16-19. VSV-G enveloped viral stocks were prepared by transfection of Plat-GP cells (Cell Biolabs) with vector DNA and VSV-G expression plasmids (pCMV-VSV-G [8454]) and concentrated 100 fold by ultracentrifugation. Parallel production of pMXs-GFP vector stocks was performed; titration of the pMXs-GFP virus was performed by infection of primary human fibroblasts and subsequent FACS analysis for GFP-expressing cells.

CF fibroblasts, plated at $10^5$ cells per well of a 6-well plate on day 0, were transduced on days 1 and 2 by spinfection (200×g for 30 minutes) at a multiplicity of infection of 21.5, in the presence of 10 micrograms/ml protamine sulfate. On day 4, fibroblasts were transferred onto irradiated mouse embryo fibroblasts (MEFs; CF-1 mouse strain, Charles River), and one day later media was switched to human embryonic stem (ES) cell media (per National Stem Cell Bank protocol SOP-CC-001C available on the internet) containing 40 ng/ml basic Fibroblast growth factor (bFGF) and re-fed daily. Starting on day 12, cells were re-fed daily with human ES cell media pre-conditioned on irradiated MEFs. Beginning at 16 days post transduction, iPS-like colonies were first identified based on morphological criteria. Live-cell staining with either Alexa 488-conjugated anti-Tra-1-60 monoclonal antibody (Stemgent) or anti-Tra-1-81 monoclonal antibody (Millipore) followed by Alexa 488 goat anti-mouse IgM (Invitrogen) was then used to identify reprogrammed colonies for subsequent expansion and characterization. Of 32 colonies originally picked (all of which stained positive for Tra-1-60 and/or Tra-1-81), 9 colonies were subsequently expanded and cryopreserved and two iPS clones (clones 17 and 28) were selected for more extensive characterization.

CF iPS cells were stained for expression of Oct4 and SSEA-4 per NSCB protocol SOP-CH-102C, and analyzed either by fluorescence microscopy or by fluorescence activated cell analysis (LSR-II, Becton Dickinson). Co-staining with anti-CD29 (FITC-conjugated; Source) was used to exclude contaminating MEFs. Non-specific alkaline phosphatase activity was also assessed (Vector Lab). Karyotyping of CF iPS clones 17 (passages 5 and 17) and 28 (passages 5 and 13) was performed at Texas Children's Hospital Clinical and Research Cytogenetic Laboratory. Genomic DNA was isolated from CF iPS clones 17 and 28; sequences containing exon 10 were amplified by PCR and sequenced.

C. Teratoma Assay

CF iPS cells (clone 17) were injected intra-muscularly into the rear dorsal leg of four week old Fox Chase SCID beige mice (Charles River) and monitored weekly for the appearance of tumor growth. At seven weeks post injection, tumors were removed, paraffin embedded, prepared for histological examination by hematoxylin and eosin, and analyzed by the Center for Comparative Medicine at Baylor College of Medicine.

D. ZFN-Mediated Targeting

Zinc finger nucleases targeted to CFTR were engineered essentially as described in U.S. Pat. No. 6,534,261. Table 1 shows the recognition helices DNA binding domain of exemplary CFTR-targeted ZFPs. The designed DNA-binding domains contain four to six zinc fingers, recognizing specified target sequences (see Table 2). Nucleotides in the target site that are contacted by the ZFP recognition helices are indicated in uppercase letters; non-contacted nucleotides indicated in lowercase.

TABLE 1

CFTR Zinc Finger Nucleases

| SBS # | Design |  |  |  |  |  |
|---|---|---|---|---|---|---|
|  | F1 | F2 | F3 | F4 | F5 | F6 |
| 12897 | WPSCLYA (SEQ ID NO: 8) | NGVLLKR (SEQ ID NO: 9) | QSGNLAR (SEQ ID NO: 10) | RSDNLSE (SEQ ID NO: 11) | NPRNRFT (SEQ ID NO: 12) | N/A |
| 9940 | RSDVLSE (SEQ ID NO: 13) | QSGNLAR (SEQ ID NO: 10) | QSGHLSR (SEQ ID NO: 14) | RSDVLSE (SEQ ID NO: 15) | WSASLSK (SEQ ID NO: 16) | N/A |
| 32365 | QNATRIN (SEQ ID NO: 17) | QSGNLAR (SEQ ID NO: 10) | RSDNLST (SEQ ID NO: 18) | QSADRKK (SEQ ID NO: 19) | N/A | N/A |

TABLE 1-continued

CFTR Zinc Finger Nucleases

| SBS # | F1 | F2 | F3 | F4 | F5 | F6 |
|---|---|---|---|---|---|---|
| 32366 | TNQNRIT (SEQ ID NO: 20) | RNQTRIT (SEQ ID NO: 21) | QSGNLAR (SEQ ID NO: 10) | QSNTRIM (SEQ ID NO: 22) | TSGNLTR (SEQ ID NO: 23) | QSNALHQ (SEQ ID NO: 24) |
| 32375 | TSSDRKK (SEQ ID NO: 25) | QSSDLSR (SEQ ID NO: 26) | DRSNLTR (SEQ ID NO: 27) | TSGNLTR (SEQ ID NO: 23) | WRLSLQV (SEQ ID NO: 28) | N/A |
| 32376 | QSGNLAR (SEQ ID NO: 10) | QGANLIK (SEQ ID NO: 29) | RSDHLSA (SEQ ID NO: 30) | ESRYLMV (SEQ ID NO: 31) | RSDNLST (SEQ ID NO: 18) | DRSNRKT (SEQ ID NO: 32) |
| 32401 | TSGNLTR (SEQ ID NO: 23) | QSNALHQ (SEQ ID NO: 24) | QSGNLAR (SEQ ID NO: 10) | TSGNLTR (SEQ ID NO: 23) | WWTSRAL (SEQ ID NO: 33) | N/A |
| 32398 | HSNARKT (SEQ ID NO: 34) | TSGNLTR (SEQ ID NO: 23) | TLQNRMS (SEQ ID NO: 35) | DQSTLRN (SEQ ID NO: 36) | N/A | N/A |

TABLE 2

CFTR Target sites

| SBS # | Target Site |
|---|---|
| 12897 | atTAGAAGtGAAGTCTGGaaataaaacc (SEQ ID NO: 37) |
| 9940 | agtgATTATGGGAGAACTGgatgttcacagtcagtccacacgtc (SEQ ID NO: 38) |
| 32365 | caTCATAGGAAACAccaaagatgatatt (SEQ ID NO: 39) |
| 32366 | atATAGATACAGAAgCGTCATcaaagca (SEQ ID NO: 40) |
| 32375 | gcTTTGATGACGCTTCTgtatctatatt (SEQ ID NO: 41) |
| 32376 | ccAACTAGAAGAGGTAAGAAactatgtg (SEQ ID NO: 42) |
| 32401 | ccTATGATGAAtATAGATacagaagcgt (SEQ ID NO: 43) |
| 32398 | acACCAATGATATTttctttaatggtgc (SEQ ID NO: 44) |

ZFN pair 12897/9940 was constructed by fusing the desired DNA binding motifs to the cleavage domain of the Fok I endonuclease. ZFNs were delivered to cells either in the form of a DNA expression plasmid or in vitro generated RNA (Epicentre and Ambion). A 1.6 kb donor containing wild-type exon 10 sequences (approximately 860 by and 290 bp of homology sequences upstream and downstream of exon 10, respectively) was originally constructed by PCR amplification of genomic DNA sequences from BAC clone RP11-1152A23. Two silent single base pair substitutions were introduced into the right ZFN binding site with the goal of interfering the ability of the introduced ZFNs to cleave the donor either prior or subsequent to homology-directed repair; an additional silent single base pair substitution was introduced into the wild-type exon 10 donor sequences in order to create a novel Cla I restriction enzyme site. Three additional single base pair changes were introduced into intron 10 donor sequences 125 by downstream of exon 10 to create a unique Avr II restriction enzyme site. All changes in the wild-type donor were introduced via Quikchange® Lightning Site-Directed Mutagenesis (Agilent). PCR amplification of pgk-puroTK-bpA sequences from plasmid pPthC-Oct3/4 (see, e.g., Masui et al. (2007) Nat Cell Biol 9:625-635) with primers including loxP recognition sequences and Avr II sites generated material for cloning into the introduced Avr II site in the CFTR donor.

ZFNs, either in the form of DNA expression plasmids (1 or 2 micrograms) or in vitro transcribed RNA (1.5 or 3 micrograms), were delivered together with donor DNA (4 or 8 micrograms) to CF iPS cells (2 million cells, cells obtained via Accutase™ treatment; clone 17) via nucleofection (Amaxa program A23) and cells were plated in the presence of 10 microM Rock-inhibitor (Alexis Biochemicals, Y27632) onto puromycin-resistant irradiated MEFs. Puromycin selection (0.5 micrograms per ml) was initiated four days post transfection, and puromycin-resistant colonies were picked starting 2-5 days later and expanded, in the presence of puromycin, to establish clonal cell lines.

E. Molecular Analysis of Targeted iPS Clones

Genomic DNA was isolated from puromycin-resistant clones beginning at passage 2 by QIAprep® Spin Miniprep Kit (Qiagen) or ArchivePure™ DNA Cell Tissue Kit (5 Prime). PCR amplification utilizing various primers was performed according to manufacturer protocols. Sequencing was performed on an ABI 3730XL sequencer.

F. Southern Blotting

In order to generate a radio-labeled DNA for probing Southern blotted genomic DNAs, the donor plasmid was digested with NdeI+SpeI, separated on 0.8% agarose gel, and then the 2.3 kb fragment was cut out and gel-purified (Qiagen). The 2.3 kb fragment was labeled with [α-$^{32}$P]dCTP using Prime-It® II Random Primer Labeling kit (Agilent Technologies) following manufacturer's instruction. 25 micrograms of genomic DNAs (gDNAs) were digested with SpeI overnight and purified by phenol/chloroform extraction. The gDNAs were then resolved on 1% agarose gel and transferred to a Nytran® Super Charge membrane (Schleicher and Schuell) and hybridized with $^{32}$P-labeled probe. The membrane was exposed and image scanned using a phosphorimager system (Molecular Dynamics).

G. Cre-Mediated Excision of Selectable Marker

Cre-expression plasmids (pBS513 EF1alpha-cre and pCAG-Cre (see, e.g., Le et al. (1999) *Anal Biochem* 270:334-336; Matsuda & Cepko (2007) *Proc Natl Acad Sci USA* 104:1027-1032) were delivered to Accutase™-treated cells via Amaxa™ nucleofection and plated onto irradiated MEFs. Individual colonies were picked and expanded, and then plated in replicate to identify those clones that had become sensitive to puromycin. Alternatively, some clones were first identified based on their resistance to FIAU (1 microM, Moravek Biochemicals), expanded, and then plated in replicate to identify puromycin sensitive clones.

H. Analysis of mRNA

RNA isolation from iPS and iPS-derived cells with the RNeasy® kit (Qiagen), cDNA synthesis was performed with Improm-II™ Reverse Transcriptase oligodT kit (Promega), and RT-PCR was performed with Gotaq Hot Start® polymerase (Promega).

I. In Vitro Differentiation

Short-term differentiation of iPS cells to definitive endoderm was conducted essentially as described in D'Amour et al. (2005) *Nat Biotechnol* 23:1534-1541. In brief, iPS cells, plated on MEFs, were exposed to Activin A (100 micrograms/ml) in the presence of low concentrations of fetal bovine serum (0& on day 0, 0.2% day 1, 2% days 2-5). Cultures were harvested for RNA on the indicated days and analyzed by RT-PCR for gene expression. For longer-term differentiation, we adapted the air liquid interface protocol reported by Van Haute et al. (2009) *Respir Res* 10:105 to generate lung epithelial tissue from human ES cells. In brief, iPS cells recovered by collagenase digestion, were plated as clumps of cells onto 8.0 micron culture plate inserts (P18P01250, Millipore) in wells of a 12-well plate previously plated with irradiated MEFs. For the first 8 days (days 0-4: human ES media; days 5-8: Differentiation Media [DM]: human ES media without beta-mercaptoethanol and basic Fibroblast growth factor) media was maintained at a level sufficient to completely cover the membrane-plated cells; from days 8 to 28, the media (DM) volume was reduced to provide the desired air liquid interface. Cultures were harvested for RNA on the indicated days and analyzed by RT-PCR for gene expression.

J. Testing of Nucleases Targeted to CFTR Mutations

Figure 6:
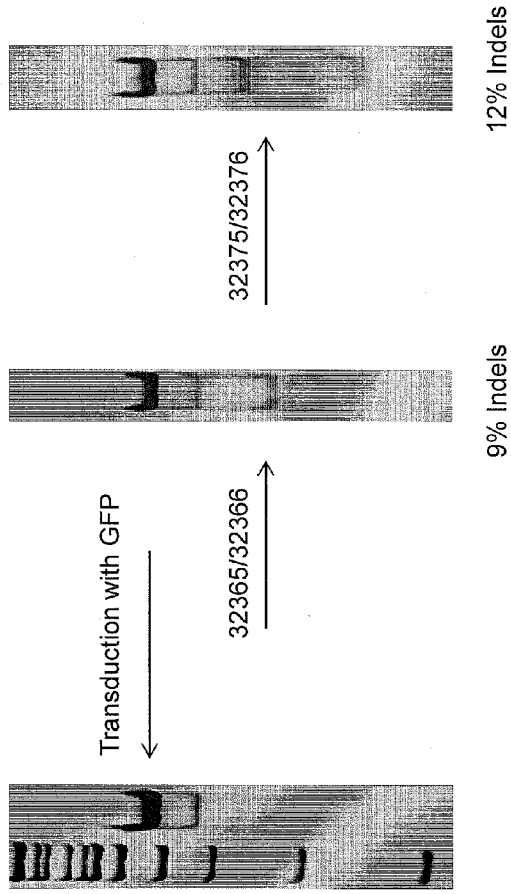
FIG. 6, panels A and B, depict additional CFTR-specific ZFNs.

ZFN pairs shown in Table 1 that were designed to be close the Δ508 mutation site include ZFN pair 12897/9940, that binds approximately 115 nt away from the site of ≠508, and pairs 32365/32366 and 32375/32376 which target sites are 18 and 48 nucleotides away, respectively. See, FIG. 6. In addition, pair 32401/32398 were designed to specifically target the Δ508 allele and not the wild type allele (see FIG. 6).

These indicated pairs were tested for nuclease activity in K562 cells and the 32365/32366 pair was found to cause a 9% measure of indel formation, and the 32375/32376 caused 12% indels. The 32401/32398 pair were tested in using the DLSSA reporter system in Neuro2A cells (see co-owned US Publication 20110301073). In this assay, the 32401/32398 pair gave a ratio of 1.45 firefly luminescence/renilla luminescence (compared to 0.16 for the pVAX vector control), demonstrating that all pairs were active.

Example 2

Derivation and Characterization of CF iPS Cells

CF primary fibroblasts (GM04320; Coriell Repository) were obtained from a patient reported homozygous for the ΔF508 CFTR mutation. Direct sequencing of exon 10 revealed these cells are actually compound heterozygous at the CFTR locus, with one allele ΔF508 and the other allele ΔI507.

Utilizing VSV-G pseudotyped pMXs retroviral vectors encoding reprogramming factors (OCT4, SOX2, KLF4, C-MYC, NANOG), we transduced the CF skin fibroblasts, transferred them onto mouse embryo fibroblasts (MEFs), and selected for reprogrammed cells in human ES cell media as described in Example 1. Beginning at 16 days post transduction, iPS-like colonies were first identified based on morphological criteria. Live-cell staining with anti-Tra-1-60 and/or anti-Tra-1-81 antibodies was then used to identify successfully reprogrammed colonies for subsequent expansion and characterization. We identified nine reprogrammed colonies, which we expanded further and cryopreserved.

Two clones (nos. 17 and 28) were selected for further study. These clones exhibited morphology and growth properties consistent with hES cells; we verified ΔI507/ΔF508 compound heterozygosity in the derived iPS cells. We also confirmed by immuno-staining that these two clones express cellular antigens characteristic of undifferentiated hES cells. By FACS analysis, we demonstrated co-expression of Oct4 and SSEA4 antigens by 90% of iPS cells for at least 33 passages. The pluripotency of the CF iPS cells was demonstrated via teratoma assay; cell types characteristic of mesoderm, ectoderm, and endoderm were present in recipient mice. We also confirmed these CF iPS cells have a normal karyotype.

Example 3

Correction of CFTR Mutation Via ZFN-Mediated HDR

Our overall strategy for correction of CFTR exon 10 mutations is outlined in FIG. 1 and included delivering CFTR-specific ZFNs together with an appropriate CFTR donor DNA; the loxP-flanked puroTK selectable cassette permits puromycin-mediated selection of initial clones as well as subsequent FIAU-mediated selection of Cre-excised clones. We designed ZFNs targeting CFTR exon 10 to facilitate the correction of either ΔI507 or ΔF508 by HDR (see, FIG. 1). The CFTR exon 10-specific ZFNs (CFTR ZFNs) recognize DNA sequences close to the start of exon 10, approximately 110 bp upstream of either the ΔI507 or ΔF508 three by deletions.

The CFTR DNA donor repair template included a total of approximately 1.6 kb of flanking homologous sequence; the donor-encoded exon 10 sequence was modified to include three silent by substitutions: two in the ZFN-R target sequence to prevent ZFN re-cleavage of the corrected CFTR locus; and a silent mutation 22 by downstream of the restored three by wild-type sequence to create a novel Cla I restriction enzyme site for the rapid identification of gene edited cells by PCR. In addition, the loxP-flanked pgk-puroTK selectable cassette was inserted, in an anti-sense orientation, into intron 10 of the donor, 125 bp downstream of the end of exon 10. Thus, the desired CFTR gene editing event would involve both the correction of the three base pair deletion in exon 10 at either the ΔI507 or ΔF508 alleles as well as targeted insertion of the selection cassette in intron 10.

Figure 2:
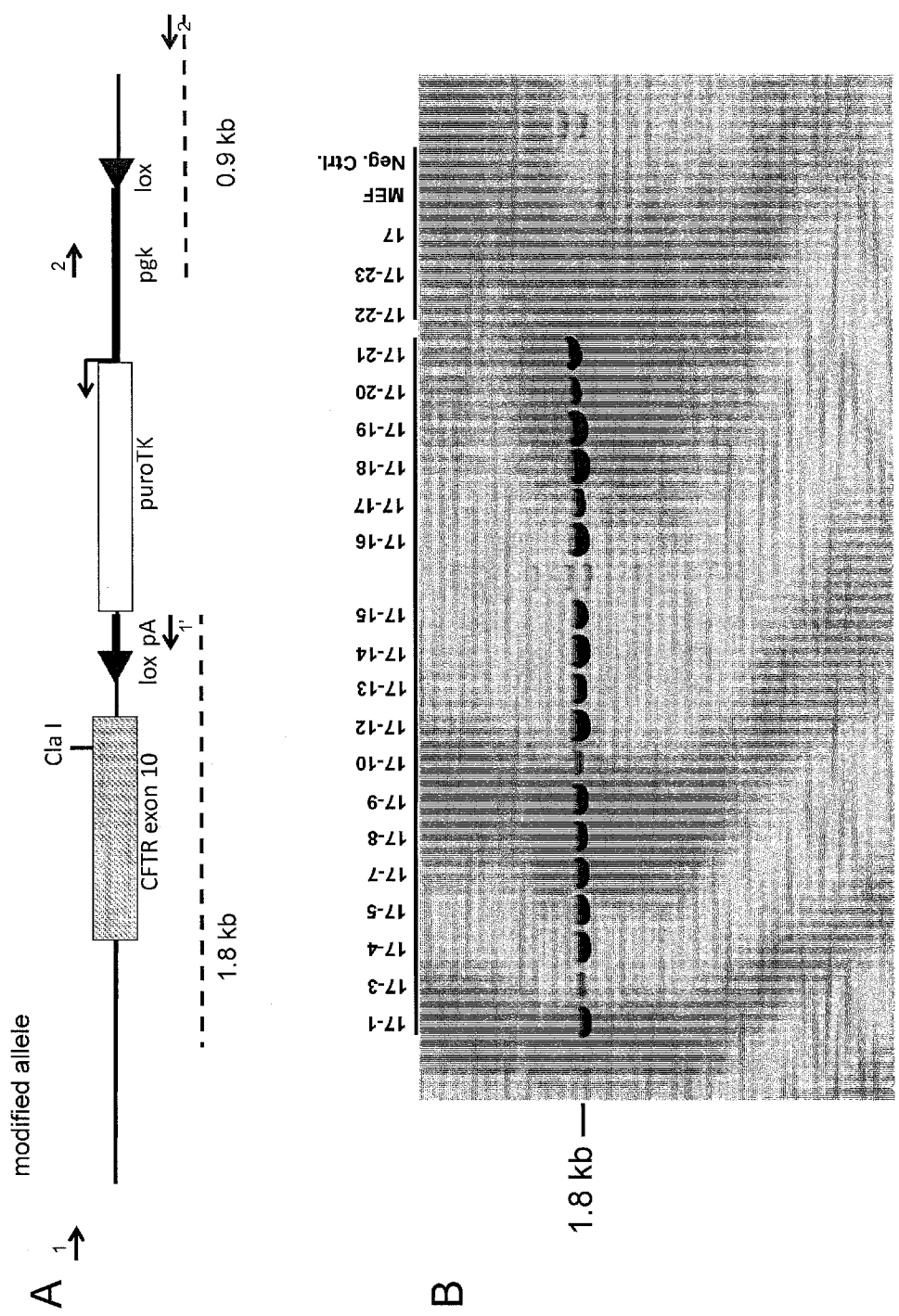
FIG. 2, panels A to C, depict ZFN-mediated genome modification in CF iPSCs.
Figure 2C:
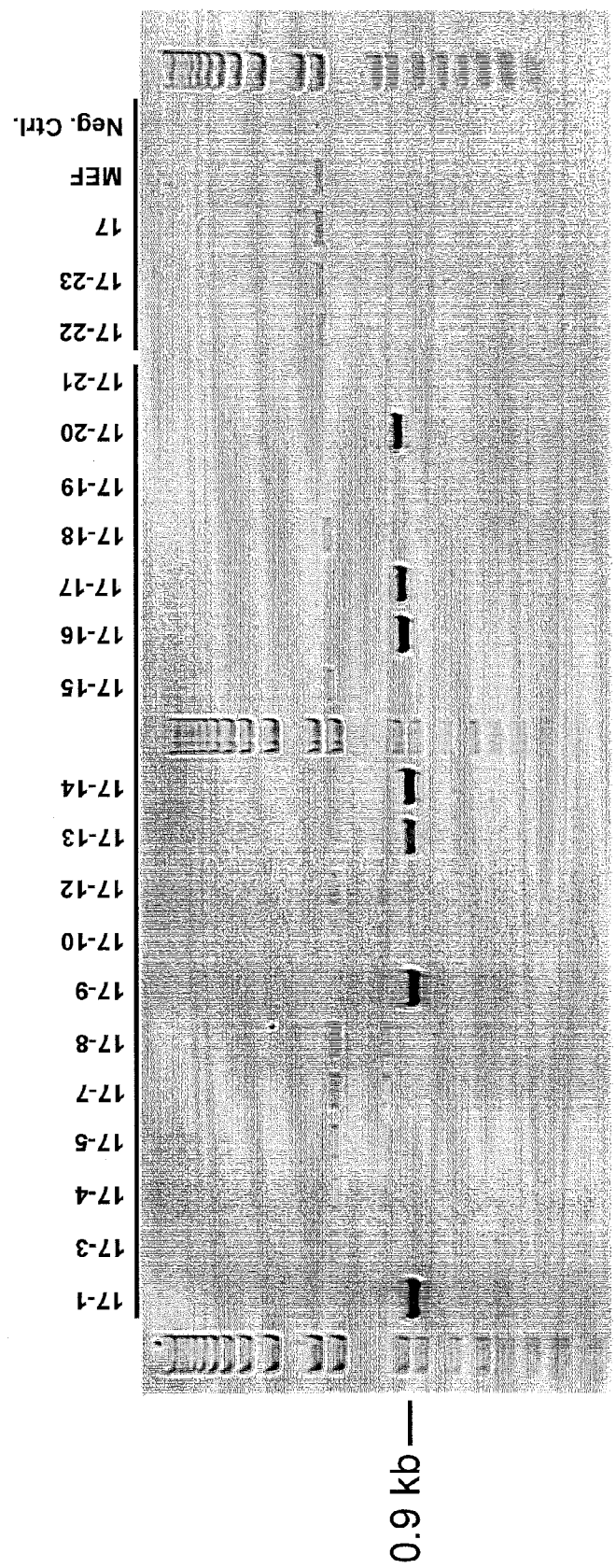
FIG. 2C is a gel depicting identification of a downstream 0.9 kb 2/2' amplicon identified in 7 CFTR-targeted iPSC clones. As shown, no 0.9 kb amplicon was identified for 11 of the previously identified 18 targeted clones, for other puroR iPS clones (clones 17-22, 17-23), for the original CF clone 17 iPSC, nor for MEFs.

The CFTR ZFNs, either in the form of DNA expression plasmids or in vitro transcribed RNA, were co-delivered with a plasmid encoding the CFTR donor to CF iPS cells as described in Example 1. Puromycin-resistant colonies were initially screened via PCR and then sequenced to confirm CFTR exon 10 was corrected via HDR (FIG. 2). The initial PCR screen assayed for targeted insertion of the puromycin selectable marker into intron 10 of the endogenous CFTR locus with one primer annealing to a sequence upstream in intron 9 (not present in the donor) and one primer annealing within the loxP-flanked selectable marker (FIG. 2).

This initial screen identified potential targeted insertion events at one of the CFTR alleles in 33% (21 out of 64 clones analyzed) of puromycin resistant colonies. This amplicon was completely digested with Cla I, consistent with incorporation of the wild-type exon 10 donor sequence. The amplicon was further analyzed by direct sequencing to verify the edited allele encoded the donor-derived corrective sequence instead of the ΔI507 or ΔF508 mutant genotypes. In addition, the silent base pair substitutions introduced into the donor at the recognition site for the right-hand ZFN were also present in the corrected allele.

Utilizing primers that anneal to sequences outside the region of homology encoded by the donor, we selectively amplified by PCR only unmodified CFTR alleles from each of the twenty-one clones. Sequencing of the unmodified allele yielded pure sequence containing either the ΔI507 mutant allele (present in 3 of 21 clones) or ΔF508 mutant allele (in 18 of 21 clones) in all clones; this result is consistent with targeted insertion of the selectable marker occurring at only one CFTR allele per clone.

The results of two gene editing experiments performed independently are shown in Table 3, where "TI" refers shows targeted integration.

TABLE 3

ZFN-mediated genomic editing of CFTR

| | # clones modified (Exp't 1) | # clones modified (Exp't 2) |
|---|---|---|
| 64 total puroR colonies analyzed | 15 | 49 |
| 21 (33%) met 1/1' criterion [3 TI in ΔF508, 18 TI in ΔI507] | 10 (2 TI in ΔF508) | 11 (1 TI in ΔF508) |
| 7 (11%) satisfied 1/1' and 2/2' criteria [all TI in DI507] | 2 | 5 |
| 4 satisfied 1/1', 2/2', and cDNA criteria [all TI in DI507] | 2 | 2 |

We further analyzed the 21 clones satisfying the 1/1' criterion by PCR amplification with one primer annealing to the loxP-flanked selectable marker and the other primer to a site downstream in intron 10 outside of the donor sequences.

As shown in FIG. 2, this analysis confirmed targeted insertion of the selectable marker in seven of the 21 previously identified clones.

As shown in Table 3, HDR-driven genome editing occurred more frequently at the ΔI507 CFTR allele than the ΔF508 allele. Accordingly, we also fully sequenced the 1.6 kb endogenous CFTR sequences, corresponding to the donor, of each mutant allele (ΔI507 or ΔF508) to examine whether there was any increased similarity of donor sequence to either mutant allele (perhaps favoring HDR in one allele vs. the other. sequencing analysis). This sequence analysis revealed a single base pair substitution (A>G) in intron 9, 76 bp upstream of the ZFN cleavage site (A>G substitution occurs at position −61 in intron 9 with respect to start of exon 10:i.e. −61A>G, present in the ΔF508 mutant allele, but absent in both the ΔI507 mutant allele and the donor. As this single base pair difference occurring selectively in the ΔF508 allele of the CF iPS cells may have caused a significant decrease in the efficiency of homology pairing and strand invasion of the ΔF508 allele and donor template. Accordingly, introducing this A>G mutation into donor sequences is expected to favor targeted correction of the ΔF508 allele.

Example 4

Expression of the Corrected CFTR Gene in Gene Edited iPS Cells and iPS-Derived Cells Expression of CFTR in ZFN-edited cells was also determined by RT-PCR and sequencing analysis. See, Example 1.

Figure 3:
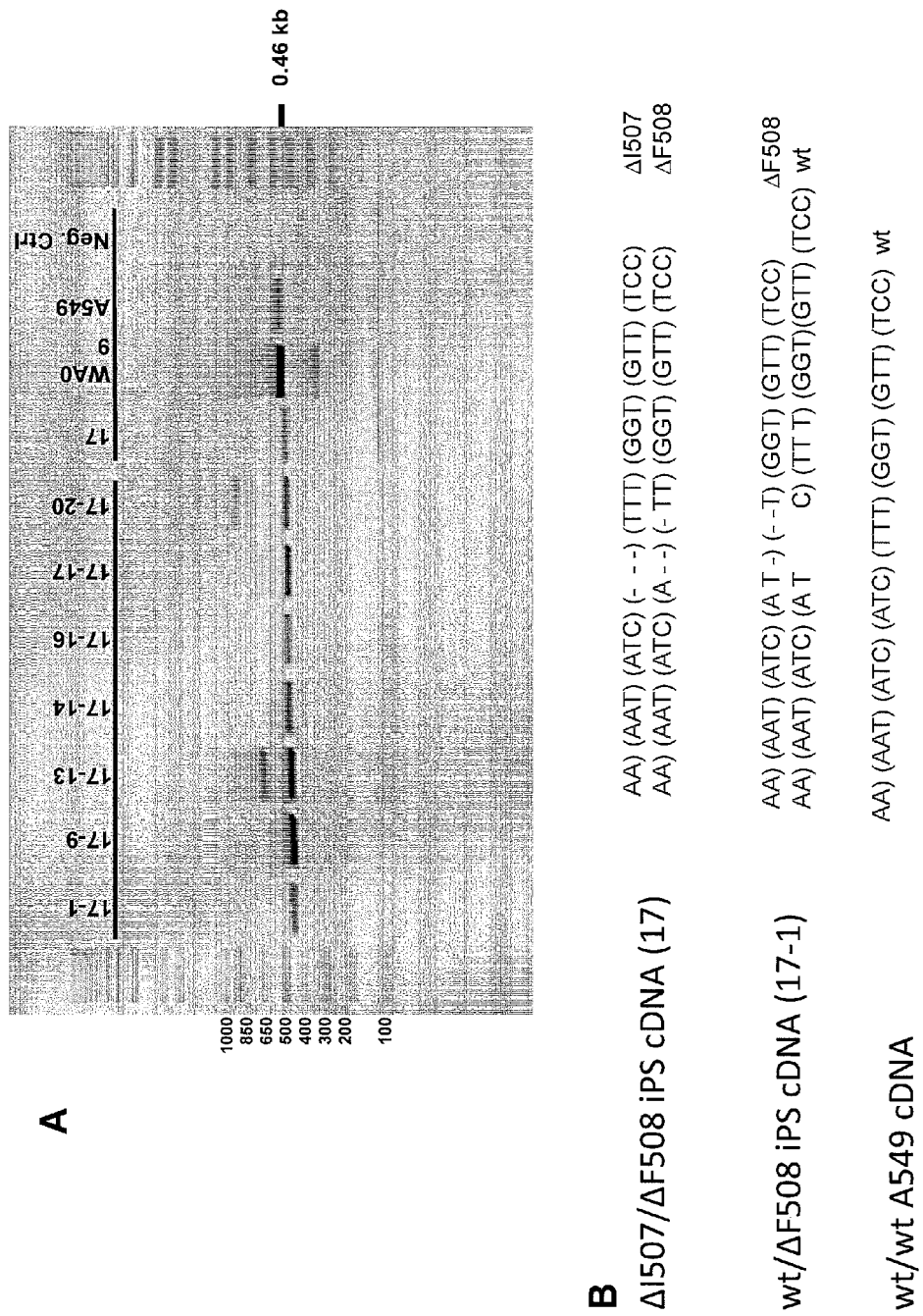
FIG. 3, panels A and B, show expression of corrected CFTR mRNA by CFTR-edited iPSC clones.

As shown in FIG. 3A, and in agreement with quantitative expression analysis of other human ES/iPS cell lines (see, e.g. Bock et al. (2011) *Cell* 144:439-452, we detected CFTR expression in the original, uncorrected ΔI507/ΔF508 Clone 17 iPS cells by RT-PCR. Sequencing demonstrated nearly equal levels of CFTR mRNA expression from both the ΔI507 and ΔF508 alleles (FIG. 3B). As a control, analysis of the A549 lung epithelial cell line confirmed wild-type CFTR expression (FIGS. 3A and 3B). As shown in FIG. 3A, RT-PCR analysis for four of the seven targeted iPS lines (Clones 17-1, 17-9, 17-14, 17-16) yielded a single band of similar size to that seen for the ΔI507/ΔF508 Clone 17 iPS and A549 cell lines; three of the seven clones (Clones 17-13, 17-17, 17-20) also exhibited a second RT-PCR band of greater size and were no longer considered for analysis.

Sequencing confirmed the expected cDNA organization (exon 9-exon 10-exon 11) and demonstrated CFTR expression arising from both the non-targeted mutant allele (ΔF508) as well as the corrected allele. See, also, FIG. 3B. In particular, we consistently observed expression of the corrected allele was approximately 25-35% of the unmodified mutant allele. CFTR genomic DNA exon 10 sequences at both targeted (in all cases ΔI507) and unmodified alleles (ΔF508) for each of these four clones were determined and Southern blot analysis was performed utilizing a pgk-puroTK probe to confirm the correct genomic organization in the corrected CFTR allele and to identify whether any of the successfully edited iPS clones also exhibited off-target integration of donor sequences.

This analysis revealed that these four clones (17-1, 17-9, 17-14, 17-16) were successfully edited without any additional integration of donor sequences; two of the clones previously eliminated (17-17 and 17-20) based on RT-PCR (see above) revealed additional pgk-puroTK integrations. Karyotypic analysis was performed on two of the correctly edited clones (17-9, 17-16) and revealed that both clonal lines exhibited a normal karyotype.

Sequencing also demonstrated all four cell lines had equivalent levels of putative novel single nucleotide variations (SNV) compared to the reference genome with 1,155 SNV in mutant CF fibroblast, 1,127 SNV in mutant iPS cells (Clone 17), 1,180 SNV in corrected 17-9-C1, and 1,121 SNV in 17-14-C1 cells. Introduced correction of the CFTR exon 10 as well as the three inserted synonymous by changes could be confirmed in both corrected, Cre-excised iPS cells (17-9-C1 and 17-14-C1) by whole genome sequencing. Overall there was no evidence for increased levels of mutations in the uncorrected iPS or corrected cell lines. We found 5 NSCV unique to iPS Clone 17, 2 NSCV unique to 17-9-C1, and 8 NSCV unique to 17-14-C1. In addition off-target ZFN binding sites, as determined as described in Cradick et al. (2011) *BMC Bioinformatics* 12:152 were only generated if each ZFN binding site was separated by 25 base pairs. Thus, there was no sequence similarity between permutations of off-target ZFN binding sites and the NSCV found in the corrected cell lines Cre-mediated excision of the pgk-puroTK cassette was achieved via transient delivery of a Cre-recombinase expression plasmid. Successful excision of the pgk-puroTK cassette was expected to result in a phenotypic conversion of clones from puro$^R$ to puro$^S$ and from FIAU$^S$ to FIAU$^R$ (FIG. 2).

Figure 4A:
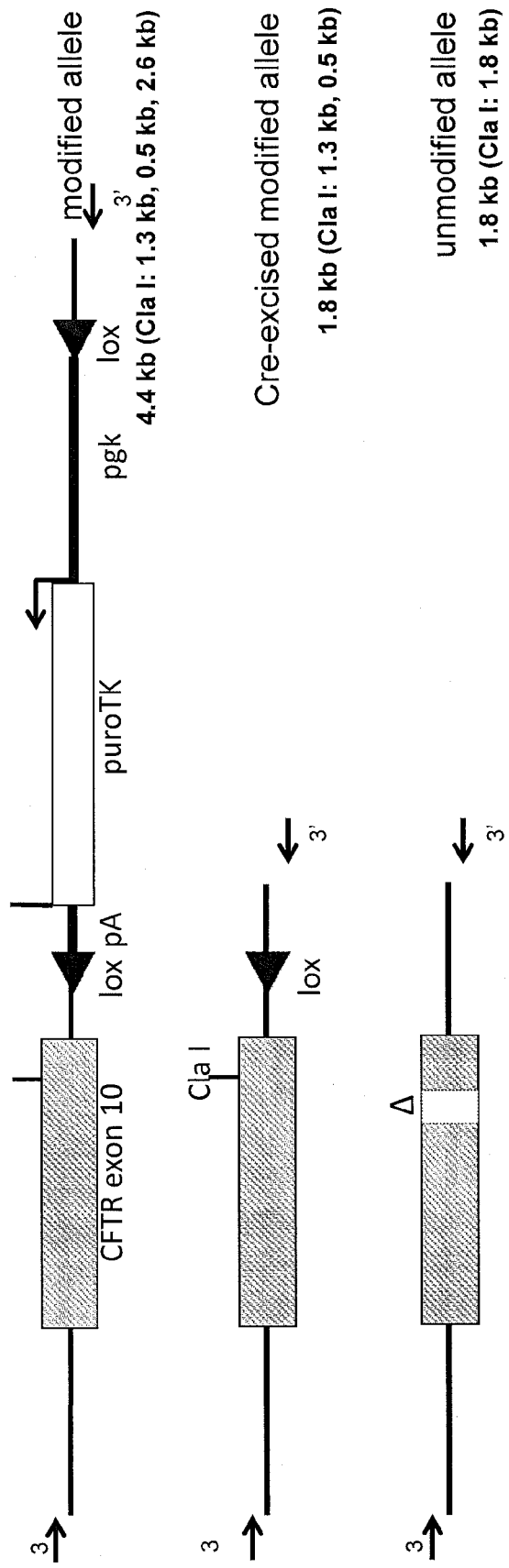
FIG. 4A is a schematic depicting the modified allele before and after Cre-mediated excision, and the unmodified allele. The location of PCR primers 3 and 3', both located outside of donor sequences, used in verification by amplification are shown. Also indicated are the expected sizes of Cla I digestion products for modified and unmodified alleles.
Figure 4B:
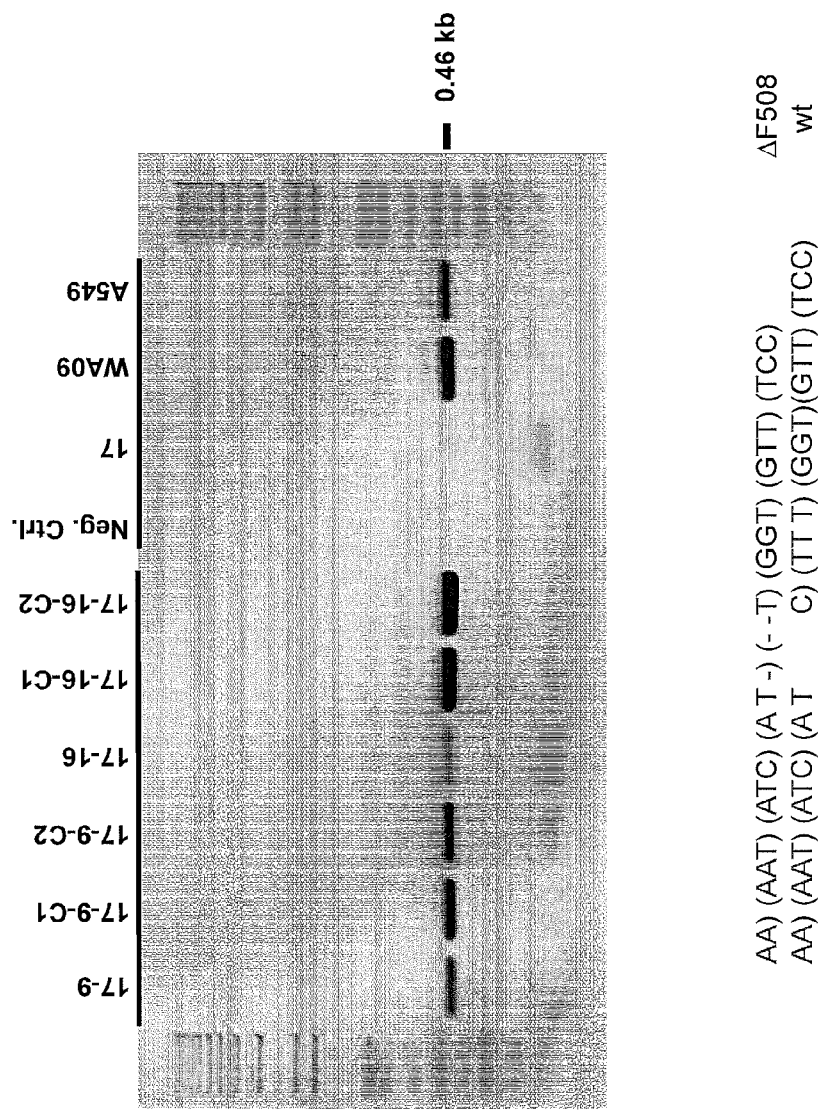
FIG. 4B is a gel showing RT-PCR analysis of CFTR expression for two targeted CF iPS clones (17-9 and 17-16) as well as their derived Cre-excised clones. Also shown is CFTR expression by the original Clone 17 CF ΔI507/ΔF508 iPS cells, WA09 hES cells, and the A549 lung epithelial cell line. Sequencing of CFTR RT-PCR product from corrected wt/ΔF508 CFTR iPS cells (Clones 17-9 and 17-16), together with Cre-excised wt/ΔF508 CFTR iPS cells (17-9-C1 and 17-9-C2; 17-16-C1 and 17-16-C2) is shown below the gel (top stand ΔF508 (SEQ ID NO:6) and bottom stand wt (SEQ ID NO:7)). Sequencing of the RT-PCR amplicon revealed equal mixture of wt and ΔF508 CFTR sequences in the Cre-excised clones.

From this process we were able to identify numerous Cre-excised clones from each of the four successfully edited clones (17-1, 17-9, 17-14, 17-16), and confirmed successful excision via PCR analysis and Cla I digestion (FIG. 4; Cre-excised clones are denoted by -C1 or -C2). As shown in FIG. 4, RT-PCR and sequencing analysis of Cre-excised clones showed approximately equal levels of CFTR mRNA expression from both the corrected and mutant alleles.

Having demonstrated expression of the corrected CFTR gene allele in corrected CF iPS cells, we next examined whether we could observe up-regulation of expression of the corrected CFTR gene under in vitro differentiation conditions. Treatment of hES/hiPS cells with Activin A has previously been shown to induce the development of definitive endoderm. See, e.g., D'Amour et al. (2005) *Nat Biotechnol* 23:1534-1541.

Figure 5:
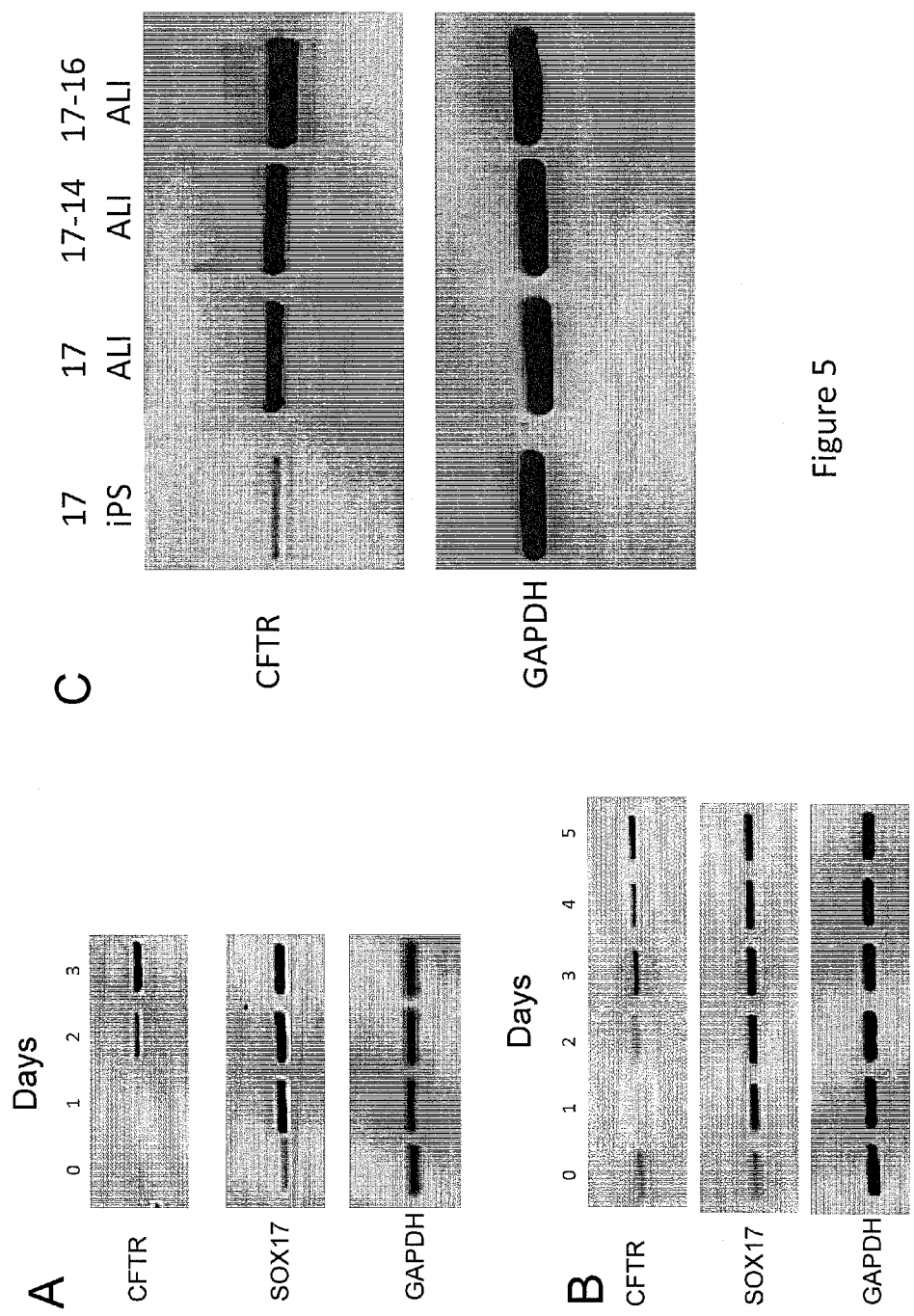
FIG. 5, panels A to C, show expression of corrected CFTR mRNA by corrected CF iPS-derived cells.

As shown in FIG. 5, the original Clone 17 CF iPS cells and corrected, Cre-excised Clone 17-9-C1 CF iPS cells, cultured in this manner for 3-5 days show evidence for up-regulation of both Sox17 and CFTR mRNAs. Sequencing of the day 5 Clone 17-9-C1 CFTR RT-PCR amplicon revealed co-expression, at approximately equal levels, of both the corrected wild-type and mutant ΔF508 CFTR mRNAs.

We also cultured the Clone 17 CF iPS cells and corrected Clone 17-14 and 17-16 CF iPS cells for 28 days in an air-liquid-interface (ALI) differentiation assay system previously shown to yield epithelial tissue with certain features (e.g. cellular composition and tissue architecture) similar to that of lung epithelium. See, e.g., Van Haute et al. (2009) *Respir Res* 10:105; Coraux et al. (2005) *Am J Respir Cell Mol Biol* 32:87-92. Under these culture conditions, CFTR expression was upregulated. Sequencing of the day 28 Clone 17-14 and 17-16 CFTR RT-PCR amplicons revealed co-equal expression of both the corrected wild-type and mutant ΔF508 CFTR mRNAs.

These results demonstrate appropriately regulated expression of the corrected CFTR allele.

Example 5

Generation of Model Systems to Study CF

Thus, the compositions and methods described herein can be used to generate model systems for the study of CF. For example, patient-derived iPSCs with corrected or disrupted ΔF508 (and/or ΔI507) provide cell and animal models to test drugs for treatment of CF.

To mitigate concerns that phenotypes observed in downstream characterization are due to variations intrinsic to the iPSC generation process (e.g. random integration of the reprogramming cassette), correction and disruption of ΔF508 is performed in a minimum of two independent iPSC lines derived from the same patient; and the same process carried out on iPSCs derived from 3 unrelated patients that carry the mutation, thereby providing isogenic cell models for studying ΔF508 mutations in the context of different genetic backgrounds.

For certain models, the CFTR ZFNs are used to introduce DSBs to the CFTR locus in iPSCs derived from normal subjects, and HDR invoked for de novo creation of monoallelic or biallelic ΔF508 mutations. The iPSCs are altered as described above, except the cells are derived from CFTR-normal subjects and the donor construct contains a nucleotide sequence that introduces the ΔF508 mutation. Clones with the expected digest pattern will be sequenced to verify the engineered mutation.

The impact of the ZFN-mediated gene editing on the CFTR protein and its activity in iPS cells is also assayed, particularly by evaluating the accumulation of CFTR in the membrane in ZFN-modified cells as compared to the corresponding unmodified cells and/or wild-type cells, using immunoblot analysis. In certain embodiments, antibodies targeted to CFTR can provide an additional readout of CFTR activity. Furthermore, reagents can be used to detect the modification of a direct target of CFTR. Having isogenic control cell lines adds great precision to these models.

Example 6

Correction of SFTPB

The most common mutation presented in SP-B deficiency is the 121ins2 (121C>GAA) mutation. Thus, ZFNs were designed to target the 121ins2 (121c>GAA) SFTPB locus as described above for the CFTR locus, and used for gene correction.

Example 7

TALEN Design and Modification of CFTR

TALEN pairs specific for the CFTR locus are also designed, and are constructed using both the canonical and novel RVDs as described in U.S. Publication 20110301073, incorporated by reference as described herein. TALENs are tested as described above and are active.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A protein comprising an engineered zinc finger protein DNA-binding domain, wherein the DNA-binding domain comprises four, five or six zinc finger recognition regions ordered F1 to F4, F1 to F5 or F1 to F6 from N-terminus to C-terminus, and wherein the protein is selected from the group consisting of:

(i) a 5-finger zinc finger protein comprising the following recognition regions:
  F1: WPSCLYA (SEQ ID NO:8);
  F2: NGVLLKR (SEQ ID NO:9);
  F3: QSGNLAR (SEQ ID NO:10);
  F4: RSDNLSE (SEQ ID NO:11); and
  F5: NPRNRFT (SEQ ID NO:12), wherein the protein binds to a target site as shown in SEQ ID NO:37;

(ii) a 5-finger zinc finger protein comprising the following recognition regions:
  F1: RSDVLSE (SEQ ID NO:13);
  F2: QSGNLAR (SEQ ID NO:10);
  F3: QSGHLSR (SEQ ID NO:14);
  F4: RSDVLSE (SEQ ID NO:15); and
  F5: WSASLSK (SEQ ID NO:16), wherein the protein binds to a target site as shown in SEQ ID NO:38;

(iii) a 4-finger zinc finger protein comprising the following recognition regions:
  F1: QNATRIN (SEQ ID NO:17);
  F2: QSGNLAR (SEQ ID NO:10);
  F3: RSDNLST (SEQ ID NO:18); and
  F4: QSADRKK (SEQ ID NO:19), wherein the protein binds to a target site as shown in SEQ ID NO:39;

(iv) a 6-finger zinc finger protein comprising the following recognition regions:
F1: TNQNRIT (SEQ ID NO:20);
F2: RNQTRIT (SEQ ID NO:21);
F3: QSGNLAR (SEQ ID NO:10);
F4: QSNTRIM (SEQ ID NO:22);
F5: TSGNLTR (SEQ ID NO:23); and
F6: QSNALHQ (SEQ ID NO:24), wherein the protein binds to a target site as shown in SEQ ID NO:40;

(v) a 5-finger zinc finger protein comprising the following recognition regions:
F1: TSSDRKK (SEQ ID NO:25);
F2: QSSDLSR (SEQ ID NO:26);
F3: DRSNLTR (SEQ ID NO:27);
F4: TSGNLTR (SEQ ID NO:23); and
F5: WRLSLQV (SEQ ID NO:28), wherein the protein binds to a target site as shown in SEQ ID NO:41;

(vi) a 6-finger zinc finger protein comprising the following recognition regions:
F1: QSGNLAR (SEQ ID NO:10);
F2: QGANLIK (SEQ ID NO:29);
F3: RSDHLSA (SEQ ID NO:30);
F4: ESRYLMV (SEQ ID NO:31);
F5: RSDNLST (SEQ ID NO:18); and
F6: DRSNRKT (SEQ ID NO:32), wherein the protein binds to a target site as shown in SEQ ID NO:42;

(vii) a 5-finger zinc finger protein comprising the following recognition regions:
F1: TSGNLTR (SEQ ID NO:23);
F2: QSNALHQ (SEQ ID NO:24);
F3: QSGNLAR (SEQ ID NO:10);
F4: TSGNLTR (SEQ ID NO:23); and
F5: WWTSRAL (SEQ ID NO:33), wherein the protein binds to a target site as shown in SEQ ID NO:43; and (viii) a 4-finger zinc finger protein comprising the following recognition regions:
F1: HSNARKT (SEQ ID NO:34);
F2: TSGNLTR (SEQ ID NO:23);
F3: TLQNRMS (SEQ ID NO:35); and
F4: DQSTLRN (SEQ ID NO:36), wherein the protein binds to a target site as shown in SEQ ID NO:44.

2. A fusion protein comprising a protein according to claim 1 and a cleavage domain.

3. The fusion protein of claim 2, wherein the cleavage domain is a cleavage half-domain.

4. The fusion protein of claim 3, wherein the cleavage half-domain is a wild-type FokI cleavage half-domain.

5. The fusion protein of claim 3, wherein the cleavage half-domain is an engineered FokI cleavage half-domain.

6. A polynucleotide encoding the protein of claim 1.

7. An isolated cell comprising the protein of claim 1.

8. An isolated cell comprising the polynucleotide of claim 6.

9. The cell of claim 7, wherein the cell is selected from the group consisting of an embryonic stem cell (ESC), a hematopoietic stem cell, a nerve stem cell, a skin stem cell, a muscle stem cell, a lung stem cell, an induced pluripotent stem cell (iPSC) and a fibroblast cell.

10. The cell of claim 8, wherein the cell is selected from the group consisting of an embryonic stem cell (ESC), a hematopoietic stem cell, a nerve stem cell, a skin stem cell, a muscle stem cell, a lung stem cell, an induced pluripotent stem cell (iPSC) and a fibroblast cell.

11. A method of modifying a cystic fibrosis transmembrane conductance regulator (CFTR) gene in an isolated cell, the method comprising;
cleaving the CFTR gene with one or more fusion proteins according to claim 2.

12. The method of claim 11, wherein the modification is selected from the group consisting of an insertion, a deletion, a substitution and combinations thereof.

13. The method of claim 11, further comprising introducing an exogenous sequence into the CFTR gene.

14. The method of claim 11, wherein the modification corrects a mutation in the CFTR gene.

15. The method of claim 14, wherein the mutation is selected from the group consisting of $\Delta$F508, $\Delta$I507 and combinations thereof.

16. A method of generating a model system for the study of cystic fibrosis (CF), the method comprising modifying cells according to the method of claim 11.

17. The method of claim 16, wherein the model system comprises a cell line.

18. The method of claim 16, wherein the model system comprises a non-human animal.

19. A kit comprising the protein according to claim 1.

* * * * *

UNITED STATES PATENT AND TRADEMARK OFFICE
CERTIFICATE OF CORRECTION

| | | |
|---|---|---|
| PATENT NO. | : 9,161,995 B2 | Page 1 of 1 |
| APPLICATION NO. | : 13/558101 | |
| DATED | : October 20, 2015 | |
| INVENTOR(S) | : Dmitry M. Guschin et al. | |

It is certified that error appears in the above-identified patent and that said Letters Patent is hereby corrected as shown below:

In the Specification

Column 1, Line 13, insert:
--U.S. GOVERNMENT SUPPORT
This invention was made with government support under Grant No. NIH RC1HL099559 awarded by the National Institutes of Health. The government has certain rights in the invention--

Signed and Sealed this
Third Day of December, 2024

Katherine Kelly Vidal
*Director of the United States Patent and Trademark Office*